United States Patent
Dake et al.

(10) Patent No.: US 10,222,334 B2
(45) Date of Patent: Mar. 5, 2019

(54) OBSERVATION DEVICE INCLUDING ILLUMINATION OPTICAL SYSTEM AND EXTRACTION UNIT AND OBSERVATION METHOD

(71) Applicant: NIKON CORPORATION, Tokyo (JP)

(72) Inventors: Fumihiro Dake, Kawasaki (JP); Tomoko Ujike, Tokyo (JP); Hiroki Yazawa, Yokohama (JP)

(73) Assignee: NIKON CORPORATION, Tokyo (JP)

( * ) Notice: Subject to any disclaimer, the term of this patent is extended or adjusted under 35 U.S.C. 154(b) by 212 days.

(21) Appl. No.: 15/275,707

(22) Filed: Sep. 26, 2016

(65) Prior Publication Data

US 2017/0082545 A1 Mar. 23, 2017

Related U.S. Application Data

(63) Continuation of application No. PCT/JP2015/001698, filed on Mar. 25, 2015.

(30) Foreign Application Priority Data

Apr. 1, 2014 (JP) ................................. 2014-075614

(51) Int. Cl.
 *G01N 21/64* (2006.01)
 *G01N 21/65* (2006.01)
 *G02B 21/00* (2006.01)
(52) U.S. Cl.
 CPC ..... *G01N 21/6458* (2013.01); *G01N 21/6445* (2013.01); *G01N 21/65* (2013.01);
 (Continued)
(58) Field of Classification Search
 CPC .................................................. G01N 21/6458
 See application file for complete search history.

(56) References Cited

U.S. PATENT DOCUMENTS

2009/0046943 A1* 2/2009 Ishiga ...................... G06T 5/10
 382/266
2011/0310475 A1* 12/2011 Iketaki ............... G01N 21/6458
 359/388

(Continued)

FOREIGN PATENT DOCUMENTS

| JP | 2009-047435 A | 3/2009 |
|----|---------------|--------|
| JP | 2013-142854 A | 7/2013 |
| JP | 2013-171154 A | 9/2013 |

OTHER PUBLICATIONS

Oct. 24, 2017 Office Action issued in Japanese Patent Application No. 2016-511371.

(Continued)

*Primary Examiner* — David P Porta
*Assistant Examiner* — Jeremy S Valentiner
(74) *Attorney, Agent, or Firm* — Oliff PLC

(57) ABSTRACT

A super-resolution observation device includes an illumination optical system collecting a first illuminating light having a first optical frequency $\omega_1$ on a first region of an observation object, collecting a second illuminating light having a second optical frequency $\omega_2'$ on a second region partially overlapping the first region, and collecting a third illuminating light having a third optical frequency $\omega_2$ on a third region containing a non-overlap region which is a region of the first region and does not overlap the second region; and an extraction unit extracting a signal light generated in accordance with a change in an energy level of a substance in the non-overlap region from a light generated in all of the first region, the second region, and the third region.

18 Claims, 14 Drawing Sheets

(52) U.S. Cl.
CPC ..... *G02B 21/0032* (2013.01); *G02B 21/0076* (2013.01); *G02B 21/0096* (2013.01); *G01N 2021/653* (2013.01); *G01N 2201/0675* (2013.01)

(56) References Cited

U.S. PATENT DOCUMENTS

| | | | | |
|---|---|---|---|---|
| 2012/0099172 A1* | 4/2012 | Ohki | ................... | G02B 21/086 |
| | | | | 359/239 |
| 2012/0257197 A1* | 10/2012 | Feldkhun | ........... | G01N 21/4795 |
| | | | | 356/301 |
| 2013/0083322 A1* | 4/2013 | Iketaki | ................... | G01N 21/65 |
| | | | | 356/301 |
| 2013/0215422 A1 | 8/2013 | Kimura et al. | | |
| 2016/0047750 A1* | 2/2016 | Berto | ..................... | G01N 21/65 |
| | | | | 356/301 |

OTHER PUBLICATIONS

Jun. 23, 2015 International Search Report issued in Japanese Patent Application No. PCT/JP2015/001698.
Oct. 4, 2016 International Preliminary Report on Patentability issued in Japanese Patent Application No. PCT/JP2015/001698.
Liu, Wei et al., "Diffraction barrier breakthrough in coherent anti-Stokes Raman scattering microscopy by additional probe-beam-induced phonon depletion.", American Physical Society, pp. 023830-1 to 023830-5, (2011).

* cited by examiner

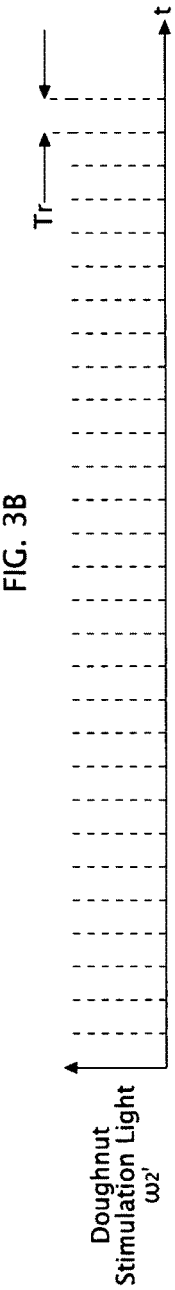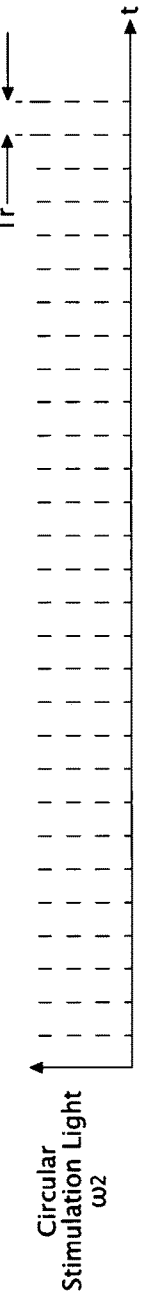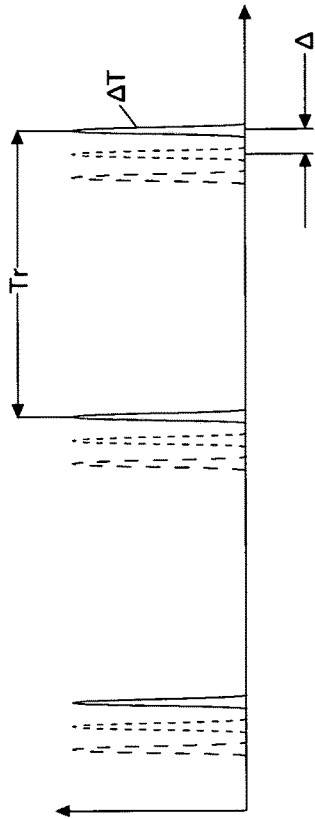
FIG. 3A
FIG. 3B
FIG. 3C
FIG. 3D

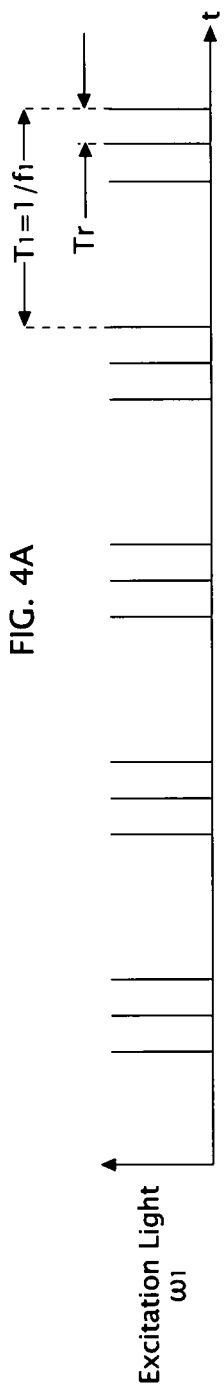
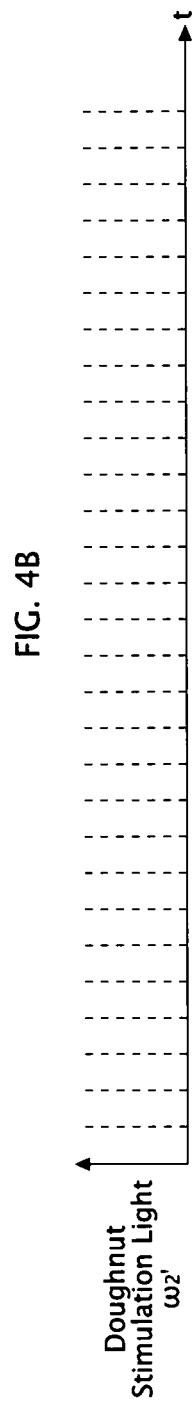
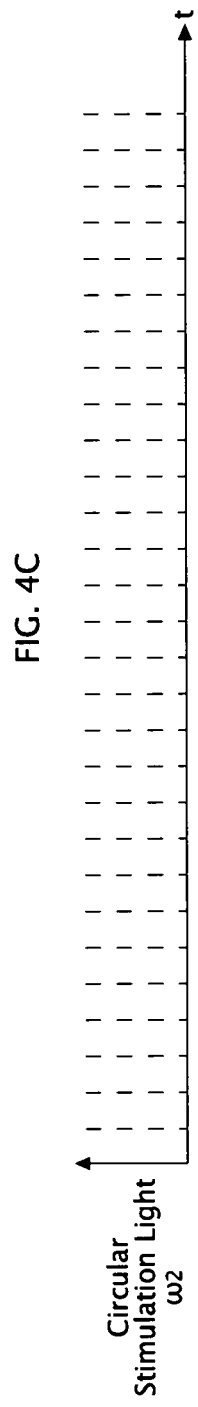
FIG. 4A
FIG. 4B
FIG. 4C

OBSERVATION DEVICE INCLUDING ILLUMINATION OPTICAL SYSTEM AND EXTRACTION UNIT AND OBSERVATION METHOD

CROSS REFERENCE TO RELATED APPLICATION

This application is a continuation application of International Application No. PCT/JP2015/001698, filed on Mar. 25, 2015, designating the U.S., in which the International Application claims a priority date of Apr. 1, 2014, based on prior filed Japanese Patent Application No. 2014-075614, the entire contents of which are incorporated herein by reference.

BACKGROUND

1. Field

The present application relates to a super-resolution observation device and a super-resolution observation method.

2. Description of the Related Art

In recent years, in the field of bioscience, particularly, molecular biology and in the field of pathological diagnosis, there has been increasing the necessity of unstained microscopy capable of performing a microscopic observation in an "intact state" without staining a sample by means of a fluorescent probe or the like. The requirements that this unstained microscopy should satisfy are mainly (1) and (2) below.
(1) High optical resolution (for example, plane resolution<50 nm and depth resolution<100 nm).
(2) Discrimination capability of an observation object inside a sample.

As a new unstained microscopy that may satisfy these requirements, a stimulated emission microscopy, a coherent anti-Stokes Raman scattering (CARS: Coherent anti-Stokes Raman scattering) microscopy, a stimulated Raman scattering (SRS: Stimulated Raman scattering) microscopy, a two-photon absorption microscopy, and the like were proposed (see Japanese Unexamined Patent Application Publication No. 2009-47435, for example).

SUMMARY

One aspect of a super-resolution observation device exemplifying the present embodiment includes an illumination optical system collecting a first illuminating light having a first optical frequency $\omega_1'$ on a first region of an observation object, collecting a second illuminating light having a second optical frequency $\omega_2'$ on a second region partially overlapping the first region, and collecting a third illuminating light having a third optical frequency $\omega_2$ on a third region containing a non-overlap region which is a region of the first region and does not overlap the second region; and an extraction unit extracting a signal light generated in accordance with a change in an energy level of a substance in the non-overlap region from a light generated in all of the first region, the second region, and the third region.

One aspect of a super-resolution observation method exemplifying the present embodiment includes collecting a first illuminating light having a first optical frequency $\omega_1$ on a first region of an observation object; collecting a second illuminating light having a second optical frequency $\omega_2'$ on a second region partially overlapping the first region; collecting a third illuminating light having a third optical frequency on a third region containing a non-overlap region which is a region of the first region and does not overlap the second region; and extracting a signal light generated in accordance with a change in an energy level of a substance in the non-overlap region from a light generated in all of the first region, the second region, and the third region.

BRIEF DESCRIPTION OF THE DRAWINGS

FIG. 3A to FIG. 3D are diagrams explaining time-variable waveforms of an excitation light, a doughnut stimulation light, and a circular stimulation light (where there is no modulation of the excitation light).

FIG. 4A to FIG. 4C are diagrams explaining time-variable waveforms of the excitation light, the doughnut stimulation light, and the circular stimulation light (where there is modulation of the excitation light).

DETAILED DESCRIPTION OF THE EMBODIMENTS

Each of conventional unstained microscopies utilizes an energy level peculiar to an observation object, to thus be able to sufficiently satisfy the requirement (2) described in Description of the Related Art, but still has room for improvement for satisfying the requirement (1), and thus the current problems exist here, Thus, the present invention provides a super-resolution observation device and a super-resolution observation method that are capable of performing a super-resolution observation on a sample without staining the sample so as to be able to solve the above-described problems.

Hereinafter, there will be explained embodiments.

First Embodiment

Hereinafter, there will be explained a stimulated emission microscopy as a first embodiment of the present invention.

Figure 1:
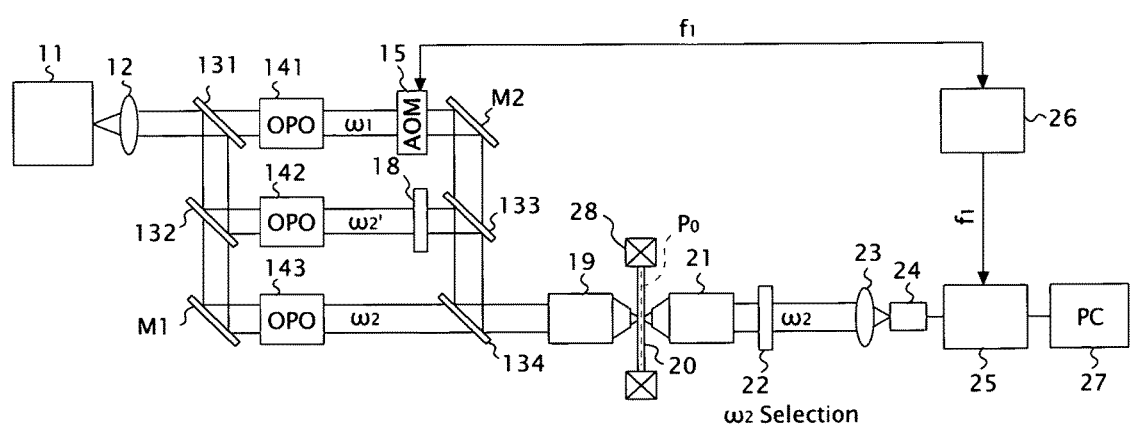
FIG. 1 is a configuration diagram of a stimulated emission microscopy of a first embodiment.

FIG. 1 is a configuration diagram of the stimulated emission microscopy of this embodiment. As illustrated in FIG. 1, in the stimulated emission microscopy, there are disposed a pulsed laser light source 11, a lens 12, beam splitters 131 and 132, a mirror M1, optical parametric oscillators (OPO: optical parametric oscillator) 141, 142, and 143, an acousto-optics modulator (AOM: Acousto-optics modulator) 15, a phase plate 18, a mirror M2, dichroic mirrors 133 and 134, an objective lens 19, a sample 20, a sample stage 28, an objective lens 21, a wavelength selection filter 22, a collecting lens 23, a light detector 24 such as a photodiode, a lock-in amplifier 25, a signal generator 26, and a personal computer 27.

The pulsed laser light source 11 is a pulsed laser light source such as a femtosecond pulsed laser light source or picosecond pulsed laser light source. A repetition frequency fr of pulse oscillation performed by the pulsed laser light source 11 is, for example, 80 MHz, and a pulse width ΔT of a pulsed laser light that the pulsed laser light source 11 oscillates is, for example, several hundred fs (femtoseconds).

A pulsed laser light exited from the pulsed laser light source 11 is turned into a collimated light flux having a large diameter by the lens 12 to be incident on the beam splitter 131. The pulsed laser light incident on the beam splitter 131 is split into a pulsed laser light that transmits through the beam splitter 131 and a pulsed laser light to be reflected by the beam splitter 131, and the pulsed laser light transmitted through the beam splitter 131 is incident on the optical parametric oscillator 141.

The pulsed laser light reflected by the beam splitter 131 is incident on the beam splitter 132, and then is split into a pulsed laser light to be reflected by the beam splitter 132 and a pulsed laser light that transmits through the beam splitter 132, and the pulsed laser light reflected by the beam splitter 132 is incident on the optical parametric oscillator 142.

The pulsed laser light transmitted through the beam splitter 132 is reflected by the mirror M1 to be incident on the optical parametric oscillator 143.

The optical parametric oscillator 141 converts an optical frequency of the incident pulsed laser light into $\omega_1$, the optical parametric oscillator 142 converts an optical frequency of the incident pulsed laser light into $\omega_2'$, and the optical parametric oscillator 143 converts an optical frequency of the incident pulsed laser light into $\omega_2$.

Here, a magnitude relation between the optical frequencies $\omega_1$, $\omega_2'$, and $\omega_2$ is $\omega_1 > \omega_2'$, $\omega_1 > \omega_2$, and $\omega_2' \sim \omega_2$. Note that it is assumed in this embodiment that such a predetermined frequency difference as to be able to wavelength—separate the light of the optical frequency $\omega_2'$ and the light of the optical frequency $\omega_2$ is provided between the optical frequencies $\omega_2$ and $\omega_2'$. This frequency difference is desired to be several nanometers or more in terms of a wavelength difference.

The acousto-optics modulator 15 is disposed in an output optical path of the optical parametric oscillator 141, namely in an independent optical path of the pulsed laser light of the optical frequency $\omega_1$, and modulates an intensity of the pulsed laser light by means of a modulation frequency $f_1$ over a time direction. Note that the modulation frequency $f_1$ of the pulsed laser light and a modulation timing by means of the acousto-optics modulator 15 are controlled by the signal generator 26.

The phase plate 18 is disposed in an output optical path of the optical parametric oscillator 142, namely in an independent optical path of the pulsed laser light of the optical frequency $\omega_2'$. A phase retardation amount distribution of this phase plate 18 is set to be non-uniform over a circumferential direction with an optical axis set as a center and uniform over a radial direction with an optical axis set as a center. Further, the phase retardation amount distribution of the phase plate 18 over the circumferential direction is a distribution such that a phase difference π is provided between two positions displaced by 180° in terms of a circumferential position. Therefore, a shape of a light spot that the pulsed laser light of the optical frequency $\omega_2'$ forms on an observation object plane $P_0$ of the sample 20 becomes a doughnut shape.

Then, the pulsed laser light of the optical frequency $\omega_1$, exited from the optical parametric oscillator 141 is reflected by the mirror M2 via the acousto-optics modulator 15, and is reflected by the dichroic mirror 134 via the dichroic mirror 133.

The pulsed laser light of the optical frequency $\omega_2'$ exited from the optical parametric oscillator 142 is reflected by the dichroic mirror 133 via the phase plate 18, and the optical path of the pulsed laser light of the optical frequency $\omega_2'$ and the optical path of the pulsed laser light of the optical frequency $\omega_1$, are combined.

The pulsed laser light of the optical frequency $\omega_2$ exited from the optical parametric oscillator 143 transmits through the dichroic mirror 134, and an optical path of the pulsed laser light of the optical frequency $\omega_2$ and the optical path of the pulsed laser light of the optical frequency $\omega_1$ and the pulsed laser light of the optical frequency $\omega_2'$ are combined.

Note that in each of the output optical paths of the optical parametric oscillators 141, 142, and 143, a not-illustrated light intensity adjusting mechanism (ND filter) is disposed. By these ND filters, an intensity of the pulsed laser light of the optical frequency $\omega_1$, an intensity of the pulsed laser light of the optical frequency $\omega_2'$, and an intensity of the pulsed laser light of the optical frequency $\omega_2$ can be adjusted independently.

The three pulsed laser lights (optical frequencies $\omega_1$, $\omega_2'$, and $\omega_2$) with a mutually combined optical path are incident on a pupil side of the objective lens 19, and then exit from the tip of the objective lens 19 to be collected onto a minute region of the observation object plane $P_0$ of the sample 20 to form light spots.

Note that the above-described phase plate 18 is disposed only in the independent optical path of the pulsed laser light of the optical frequency $\omega_2'$ out of the pulsed laser light of the optical frequency $\omega_1$, the pulsed laser light of the optical frequency $\omega_2'$, and the pulsed laser light of the optical frequency $\omega_2$. Therefore, the light spot that the pulsed laser light of the optical frequency $\omega_1$ forms on the observation object plane $P_0$ is circular, the light spot that the pulsed laser light of the optical frequency $\omega_2'$ forms on the observation object plane $P_0$ is a doughnut-shape (ring-belt shape), and the light spot that the pulsed laser light of the optical frequency $\omega_2$ forms on the observation object plane $P_0$ is circular.

Here, in the stimulated emission microscopy of this embodiment, a relation between an optical path length of the pulsed laser light of the optical frequency $\omega_1$, an optical path length of the pulsed laser light of the optical frequency $\omega_2'$, and an optical path length of the pulsed laser light of the optical frequency $\omega_2$ is adjusted beforehand so that the order in which they are emitted to the observation object plane $P_0$ becomes an order below.

(1) The pulsed laser light of the optical frequency $\omega_1$
(2) The pulsed laser light of the optical frequency $\omega_2'$
(3) The pulsed laser light of the optical frequency $\omega_2$ Among the above, the circular light spot that the pulsed laser light of the optical frequency $\omega_1$ forms on the observation object plane $P_0$ has a function of shifting an energy level of electrons of a specific observation object substance to an excitation level (excitation), the doughnut-shaped light spot that the pulsed laser light of the optical frequency $\omega_2'$ forms on the observation object plane $P_0$ has a function of shifting the excited electrons to a base level (stimulated emission) to generate a stimulated emission light, and the circular light spot that the pulsed laser light of the optical frequency $\omega_2$ forms on the observation object plane $P_0$ has a function of transforming the excited electrons that are not stimulated emitted by the pulsed laser light of the optical frequency $\omega_2'$ to a ground state (stimulated emission) to generate a stimulated emission light.

Note that the optical frequency $\omega_1$ is desirably set to a value within a range of from ultraviolet region to visible region wavelengths approximately in terms of a wavelength, and the optical frequencies $\omega_2$ and $\omega_2'$ are each desirably set to a value within a range of from ultraviolet region to near-infrared region wavelengths approximately in terms of a wavelength.

Figure 2A:
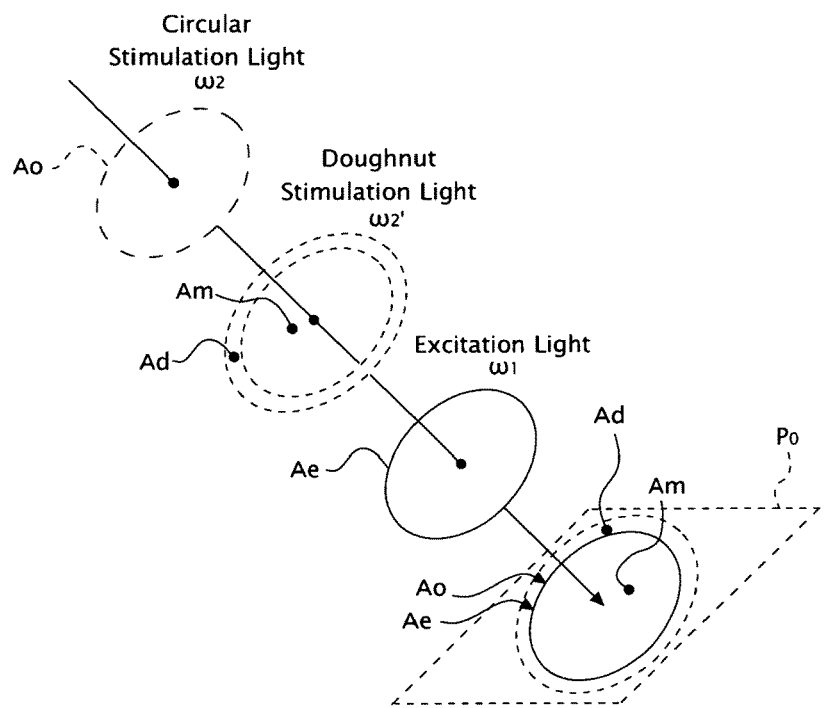
FIG. 2A and FIG. 2B are diagrams explaining a relation between an excitation light spot, a doughnut stimulation light spot, and a circular stimulation light spot.

Thus, in the following, as illustrated in FIG. 2A, the pulsed laser light of the optical frequency $\omega_1$ to be emitted to the observation object plane $P_0$ first is referred to as an "excitation light", the pulsed laser light of the optical frequency $\omega_2'$ to be emitted there next is referred to as a "doughnut stimulation light", and the pulsed laser light of the optical frequency $\omega_2$ to be emitted there finally is referred to as a "circular stimulation light". Note that in FIG. 2A, each of the light spots formed on the observation object plane $P_0$ is illustrated in a manner to be displaced in an optical axis direction.

Further, in the following, a circular region of the observation object plane $P_0$ where the excitation light is emitted is referred to as an "excitation light spot", a doughnut-shaped region of the observation object plane $P_0$ where the doughnut stimulation light is emitted is referred to as a "doughnut stimulation light spot", and a circular region of the observation object plane $P_0$ where the circular stimulation light is emitted is referred to as a "circular stimulation light spot".

Note that as illustrated in FIG. 2A, a counter of an excitation light spot Ae, an inner counter of a doughnut stimulation light spot Ad, and a contour of a circular stimulation light spot Ao substantially coincide with each other basically. This is because sizes of these contours are substantially determined by a diffraction limit.

Figure 2B:
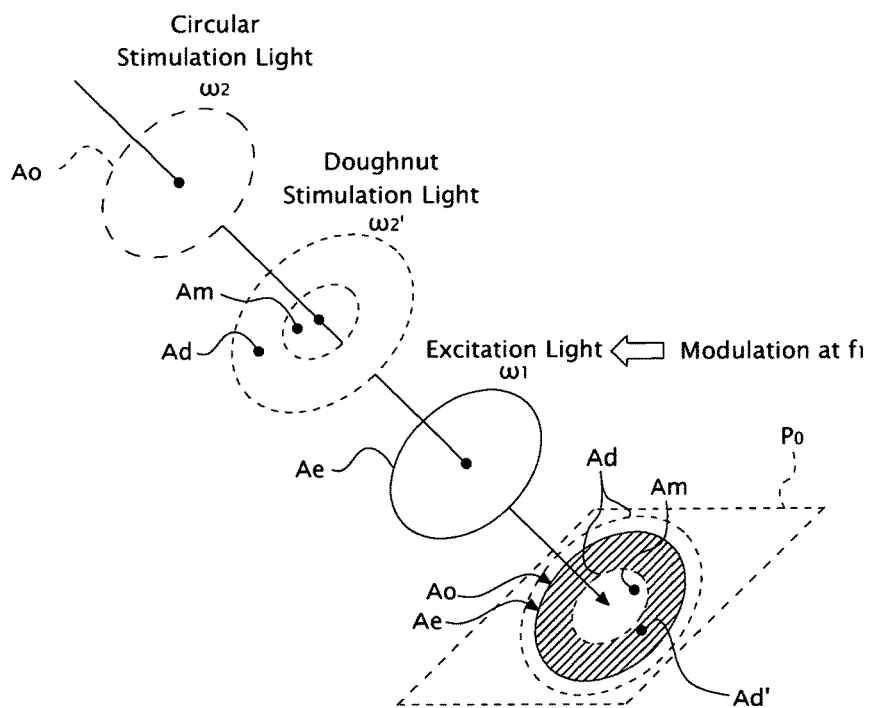

However, in this embodiment, as illustrated in FIG. 2B, the intensity of the doughnut stimulation light is set sufficiently high so as to make the inner contour of the doughnut stimulation light spot Ad become smaller than the contour of the excitation light spot Ae.

Therefore, in this embodiment, for example, a transmittance of the ND filter inserted in the independent optical path of the doughnut stimulation light is set high. Alternatively, each reflection ratio of the beam splitters 131 and 132 is set high.

Accordingly, in this embodiment, the doughnut stimulation light spot Ad overlaps the excitation light spot Ae in a doughnut-shaped region Ad' as indicated by oblique lines given at the lower right in FIG. 2B.

Hereinafter, the doughnut-shaped region Ad' that overlaps the doughnut stimulation light spot Ad in the excitation light spot Ae is referred to as an "overlap region Ad'", and a circular region Am that does not overlap the doughnut stimulation light spot Ad in the excitation light spot Ae is referred to as a "non-overlap region Am". In this embodiment, a detection origin of a signal light (an observation object point) is limited only to this non-overlap region Am, thereby obtaining a super-resolution effect.

Note that limiting the detection origin of a signal light to a region (the non-overlap region Am) smaller than the size determined by a diffraction limit (size of the excitation light spot Ae) is referred to as "super resolution" here.

Further, in the following, a set of the excitation light spot Ae, the doughnut stimulation light spot Ad, and the circular stimulation light spot Ao is referred to as a "light spot" simply.

FIG. 3A illustrates a time waveform of the excitation light, FIG. 3B illustrates a time waveform of the doughnut stimulation light, and FIG. 3C illustrates a time waveform of the circular stimulation light.

As illustrated in FIG. 3A to FIG. 3C, a repetitive pitch Tr of a pulse is common between the excitation light, the doughnut stimulation light, and the circular stimulation light, but a timing at which a pulse reaches the observation object plane $P_0$ differs by a slight amount between the excitation light, the doughnut stimulation light, and the circular stimulation light. FIG. 3D is one where waveforms of three pulses of each of the excitation light, the doughnut stimulation light, and the circular stimulation light are illustrated on the same coordinates in an enlarged manner. In FIG. 3D, one indicated by a solid line is a pulse of the excitation light, one indicated by a fine dotted line is a pulse of the doughnut stimulation light, and one indicated by a large dotted line is a pulse of the circular stimulation light. As illustrated in FIG. 3D, a difference Δ between the timing of the pulse of the excitation light reaching the observation object plane $P_0$, the timing of the pulse of the doughnut stimulation light reaching the observation object plane $P_0$, and the timing of the pulse of the circular stimulation light reaching the observation object plane $P_0$ is set to an extent slightly larger than a pulse width ΔT of each of the excitation light, the doughnut stimulation light, and the circular stimulation light, for example, several hundred fs (femtoseconds).

Here, the difference Δ is desired to be a period when electrons of the observation object substance can maintain an excited state (a lifetime of excited state, for example, about femtosecond to picosecond) or less. Thereby, the stimulated emission occurs securely. Further, in this case, the pulse width ΔT is also desired to be the lifetime of excited state or less. This makes it possible to securely separate pulses adjacent to each other in terms of time while maintaining the difference Δ to the lifetime of excited state or less.

Note that in order to adjust the difference Δ between the timings of the excitation light, the doughnut stimulation light, and the circular stimulation light reaching the observation object plane $P_0$, in the stimulated emission microscopy of this embodiment, an optical path length adjusting mechanism made of a movable mirror and the like (not illustrated) is desirably provided in at least two optical paths out of the independent optical path of the excitation light, the independent optical path of the doughnut stimulation light, and the independent optical path of the circular stimulation light.

Further, although in FIG. 3A to FIG. 3C, modulation of the excitation light performed by the acousto-optics modulator 15 is not visualized, visualization of the modulation is as illustrated in FIG. 4A to FIG. 4C. As illustrated in FIG. 4A, the modulation frequency $f_1$ of the excitation light by means of the acousto-optics modulator 15 is sufficiently low as compared to the repetition frequency fr of a pulse and satisfies $f_1 \leq fr/2$, where, for example, $f_1$ is several MHz or so. Note that in FIG. 4A, a symbol $T_1$ denotes a modulation pitch of the excitation light (=a reciprocal of the modulation frequency $f_1$), and a symbol Tr denotes the repetitive pitch of a pulse (=a reciprocal of the repetition frequency fr).

Then, returning to FIG. 1, the sample 20 is, for example a transparent living cell contained in an incubation container together with a culture fluid, and a specific substance in this living cell (for example, a specific protein such as hemoglobin) is the observation object substance. The stimulated emission microscopy utilizes an energy level peculiar to the observation object substance, so that the observation object substance does not have to be fluorescently stained beforehand.

The sample stage 28 is a transmission-type stage that supports the sample 20, moves the sample 20 over the optical axis direction (a z direction), and at the same time, moves the sample 20 over a direction perpendicular to the optical axis (an XY direction). When the sample stage 28 moves the sample 20 over the Z direction, a depth of the observation object plane $P_0$ inside the sample 20 is adjusted, and when the sample stage 28 moves the sample 20 over the XY direction, the observation object plane $P_0$ can be two-dimensionally scanned in the aforementioned light spot (at the observation object point in the spot).

Lights exited from the light spot of the observation object plane $P_0$, namely the excitation light exited from the light spot, the doughnut stimulation light exited from the light spot, the circular stimulation light exited from the light spot, and the stimulated emission light generated in the light spot are incident on the objective lens 21 from a tip side of the objective lens 21.

Specifications (a numerical aperture, a magnification, and the like) of the objective lens 21 are the same as those of the objective lens 19, and a locational relationship and an attitude relationship between the objective lens 21 and the objective lens 19 are symmetrical with respect to the observation object plane $P_0$. Note that the specifications of the objective lens 21 and the specifications of the objective lens 19 are made common here, but it is acceptable that they are not common completely. For example, a numerical aperture of the objective lens 21 may be larger than a numerical aperture of the objective lens 19.

The lights incident on the objective lens 21 from the tip side, namely the excitation light, the doughnut stimulation light, the circular stimulation light, and the stimulated emission light that are exited from the light spot of the observation object plane $P_0$ exit from a pupil side of the objective lens 21 to then head toward the light detector 24 via the wavelength selection filter 22 and the collecting lens 23 in order.

However, the wavelength selection filter 22 includes wavelength-selectivity characteristics that cause the wavelength selection filter 22 to block lights of the optical frequencies $\omega_1$ and $\omega_2'$ and allow a light of the optical frequency $\omega_2$ to pass therethrough provided thereto.

Therefore, the excitation light (optical frequency $\omega_1$) exited from the light spot and the doughnut stimulation light (optical frequency $\omega_2'$) exited from the light spot are not incident on the light detector 24, and the circular stimulation light (optical frequency $\omega_2$) exited from the light spot and the stimulated emission light (optical frequency $\omega_2$) generated in the light spot are incident on the light detector 24.

The light detector 24 is a photoelectric conversion element that converts an intensity of incident light into an electrical signal, such as a photodiode.

The lock-in amplifier 25 lock-in detects, from the electrical signal output from the light detector 24, a component to change by means of the same frequency as the modulation frequency $f_1$ of the excitation light as a signal. Note that a detection frequency and a detection timing of the lock-in amplifier 25 are controlled by the signal generator 26.

The personal computer 27 takes in the signal detected by the lock-in amplifier 25. Further, the personal computer 27, during the aforementioned scanning, performs taking-in of a signal when the observation object point is located at each position of the observation object plane $P_0$, and acquires a distribution of signals on the observation object plane as a stimulated emission image, and then displays it on a not-illustrated monitor.

Hereinafter, there will be explained a stimulated emission process of this embodiment in detail with reference to FIG. 2B.

First, in this embodiment, when the excitation light is emitted to the observation object plane $P_0$, the energy level of electrons of the observation object substance located in the excitation light spot Ae shifts to the excitation level (excitation).

Subsequently, when the doughnut stimulation light is emitted to the observation object plane $P_0$, in the overlap region Ad', the energy level of the excited electrons returns to the base level, but in the non-overlap region Am, the energy level of the excited electrons does not change at all.

Subsequently, when the circular stimulation light is emitted to the observation object plane $P_0$, in the overlap region Ad', there exist no excited electrons, and thus the stimulated emission does not occur, but in the non-overlap region Am, the energy level of the excited electrons returns to the base level and a stimulated emission light is generated.

Accordingly, in the stimulated emission microscopy of this embodiment, by emitting the doughnut stimulation light, a detection origin of the stimulated emission light (an acquisition origin of the signal) is limited only to the non-overlap region Am that is smaller than a resolution limit of the objective lens 19 (the size of excitation light spot Ae). Accordingly, the stimulated emission microscopy of this embodiment can perform a super-resolution observation of the sample 20.

Hereinafter, the lock-in detection of this embodiment will be explained.

Normally, in the stimulated emission microscopy, between a stimulated emission light generated in a sample in response to a stimulation light, (which will be referred to as a "signal light" hereinafter), and a stimulation light exited from the sample, (which will be referred to as a "noise light"

hereinafter), their optical frequency is common ($\omega_2$) and their propagation direction is also common, so that separation of the signal light and the noise light cannot be performed by the wavelength selection filter.

Therefore, in the stimulated emission microscopy of this embodiment, as described above, the intensity of excitation light is modulated by means of the frequency $f_1$ in the acousto-optics modulator 15, and at the same time, the component to change by means of the frequency $f_1$ is lock-in detected from the electrical signal output from the light detector 24 in the lock-in amplifier 25.

Figure 5A:
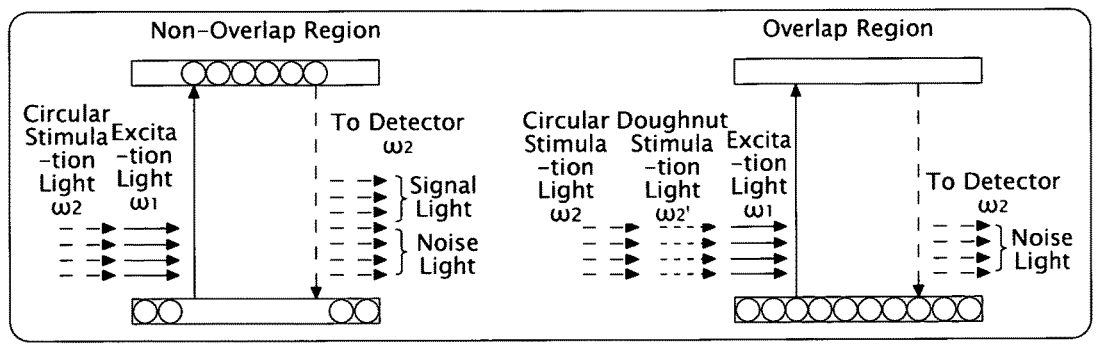
FIG. 5A and FIG. 5B are diagrams explaining lights (a signal light and a noise light) to be incident on a light detector 24.
Figure 5B:
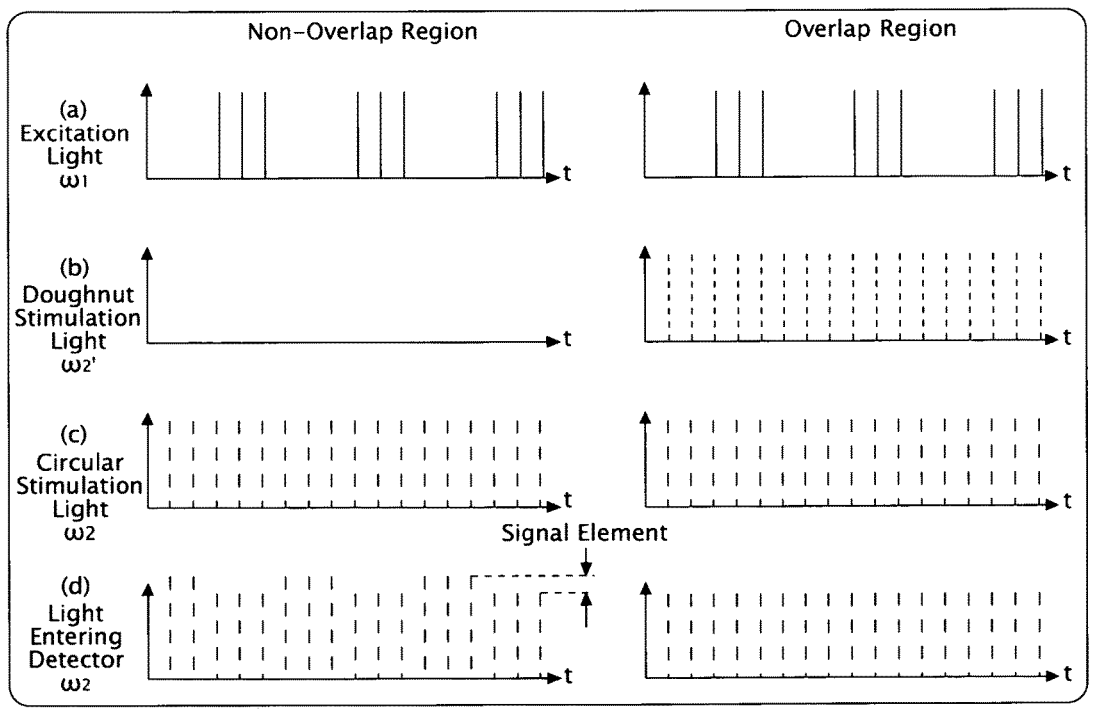

FIG. 5A and FIG. 5B are diagrams explaining lights to be incident on the light detector 24. FIG. 5A is a diagram explaining a relation between the stimulated emission process and the lights to be incident on the light detector 24, and FIG. 5B is a diagram explaining a relation between respective waveforms of the excitation light, the doughnut stimulation light, and the circular stimulation light and a waveform of the light to be incident on the light detector 24.

Further, on the left side of FIG. 5A and FIG. 5B, the lights heading toward the light detector 24 from the non-overlap region Am are explained, and on the right side of FIG. 5A and FIG. 5B, the light heading toward the light detector 24 from the overlap region Ad' is explained. Note that although in FIG. 5A and FIG. 5B, the lights from the non-overlap region Am and the light from the overlap region Ad' are illustrated distinctively, the lights from the non-overlap region Am and the light from the overlap region Ad' are incident on the actual light detector 24 with no distinction.

First, as illustrated on the left side of FIG. 5A, the doughnut stimulation light is not emitted to the non-overlap region Am, so that generation of the signal light is not suppressed at all. Therefore, the lights heading toward the light detector 24 from the non-overlap region Am are both the signal light and the noise light.

In the meantime, as illustrated on the right side of FIG. 5A, the doughnut stimulation light is emitted to the overlap region Ad', so that generation of the signal light is suppressed. Therefore, the light heading toward the light detector 24 from the overlap region Ad' is only the noise light.

Then, in this embodiment, as illustrated in (a) of FIG. 5B, the excitation light is modulated by means of the frequency $f_1$. An amount of the signal light changes in response to the intensity of excitation light, while an amount of the noise light does not depend on the intensity of excitation light.

Accordingly, as illustrated on the left side of (d) of FIG. 5B, modulation by means of the frequency $f_1$ is transcribed in the waveform of the lights heading toward the light detector 24 from the non-overlap region Am (a modulation amount becomes an amount in response to the intensity of signal light), while as illustrated on the right side of (d) of FIG. 5B, modulation by means of the frequency $f_1$ is not transcribed in the waveform of the light heading toward the light detector 24 from the overlap region Ad'.

Accordingly, it is obvious that the signal to change by means of the frequency $f_1$ is lock-in detected from the electrical signal output from the light detector 24 like this embodiment, thereby making it possible to detect the intensity of signal light with high accuracy (that is the explanation of the lock-in detection).

Note that in this embodiment, the doughnut stimulation light and the circular stimulation light are wavelength-separated in order to block the doughnut stimulation light exited from the light spot of the observation object plane $P_0$ before the light detector 24. That is, a difference is provided between the optical frequency of the doughnut stimulation light and the optical frequency of the circular stimulation light that head toward the observation object plane $P_0$, and at the same time, the wavelength selection filter 22 that blocks a light of the same optical frequency as that of the doughnut stimulation light and allows a light of the same optical frequency as that of the circular stimulation light to pass therethrough is disposed before the light detector 24.

In this embodiment, however, instead of wavelength-separating the doughnut stimulation light and the circular stimulation light, the doughnut stimulation light and the circular stimulation light may be polarization-separated. That is, it is also possible to provide, between a polarization direction of the doughnut stimulation light heading toward the observation object plane $P_0$ and a polarization direction of the circular stimulation light heading toward the observation object plane, a difference, and at the same time, dispose, before the light detector 24, an analyzer that blocks a light in the same polarization direction as that of the doughnut stimulation light and allows a light in the same polarization direction as that of the circular stimulation light to pass therethrough (see a modified example below).

Modified Example of First Embodiment

Hereinafter, there will be explained a modified example of the first embodiment. Here, only differences from the first embodiment (FIG. 1) are explained.

Figure 6:
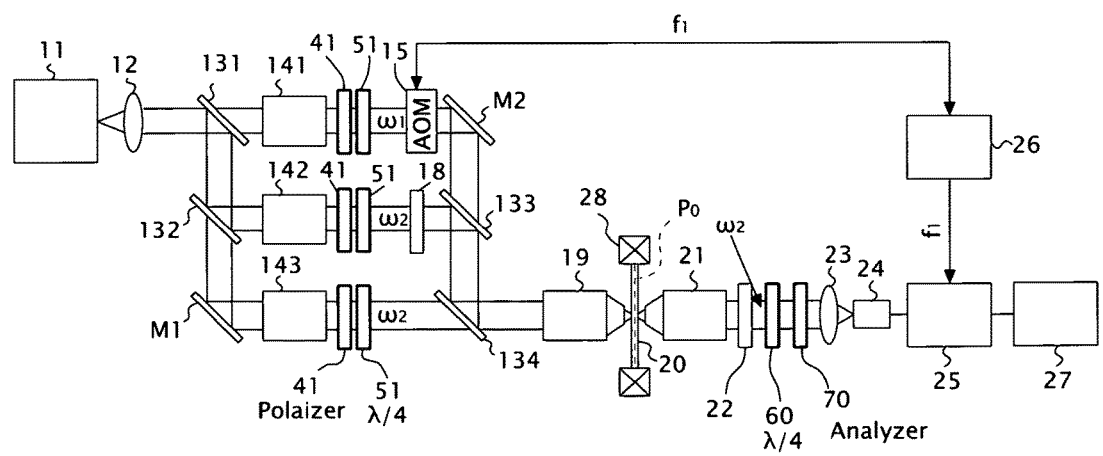
FIG. 6 is a configuration diagram of a stimulated emission microscopy of a modified example.

FIG. 6 is a configuration diagram of a stimulated emission microscopy of the modified example.

First, in the stimulated emission microscopy of the modified example, the optical frequency of the doughnut stimulation light is set to the same as the optical frequency $\omega_2$ of the circular stimulation light.

Further, in the stimulated emission microscopy of the modified example, the wavelength selection filter 22 includes wavelength-selectivity characteristics that cause the wavelength selection filter 22 to block a light of the optical frequency $\omega_1$ and allow a light of the optical frequency $\omega_2$ to pass therethrough provided thereto.

Further, in the stimulated emission microscopy of the modified example, in each of the independent optical path of the excitation light, the independent optical path of the doughnut stimulation light, and the independent optical path of the circular stimulation light, a polarizer 41 and a ¼ wavelength plate 51 are disposed in order, and between the objective lens 21 and the collecting lens 23, a ¼ wavelength plate 60 and an analyzer 70 are disposed in order.

Figure 7:
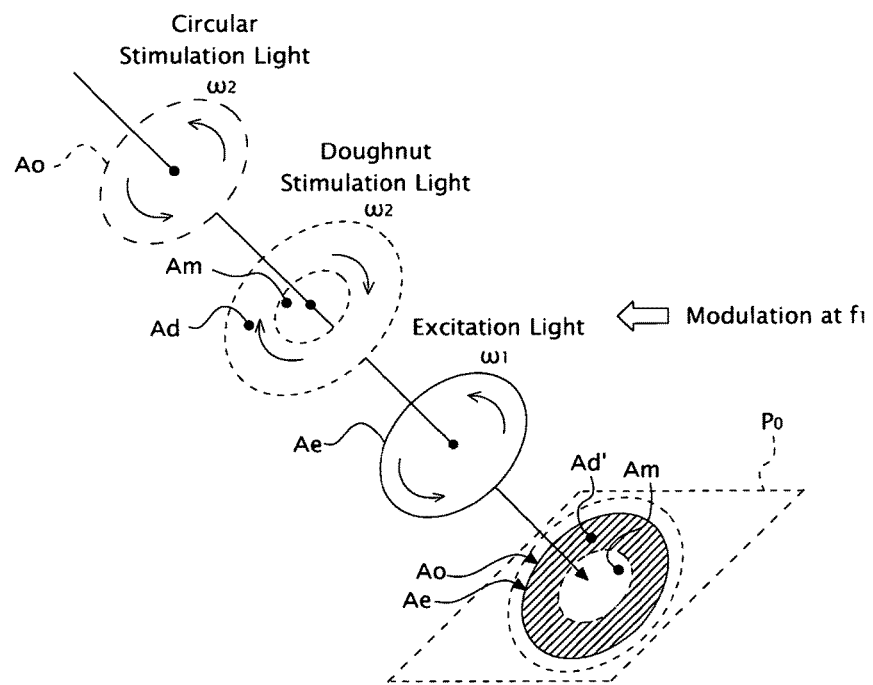
FIG. 7 is a diagram explaining a relation between the excitation light spot, the doughnut stimulation light spot, and the circular stimulation light spot in the stimulated emission microscopy of the modified example.

Further, in the stimulated emission microscopy of the modified example, axis directions of the polarizers 41 and the ¼ wavelength plates 51 are adjusted beforehand, and as illustrated in FIG. 7, polarized states of the excitation light and the circular stimulation light to be incident on the observation object plane $P_0$ are set to circular polarization in which they circle in the same direction (for example, right-handed circular polarization), and a polarized state of the doughnut stimulation light to be incident on the observation object plane $P_0$ is set to circular polarization in which it circles inversely to the excitation light and the circular stimulation light (for example, left-handed circular polarization).

Figure 8:
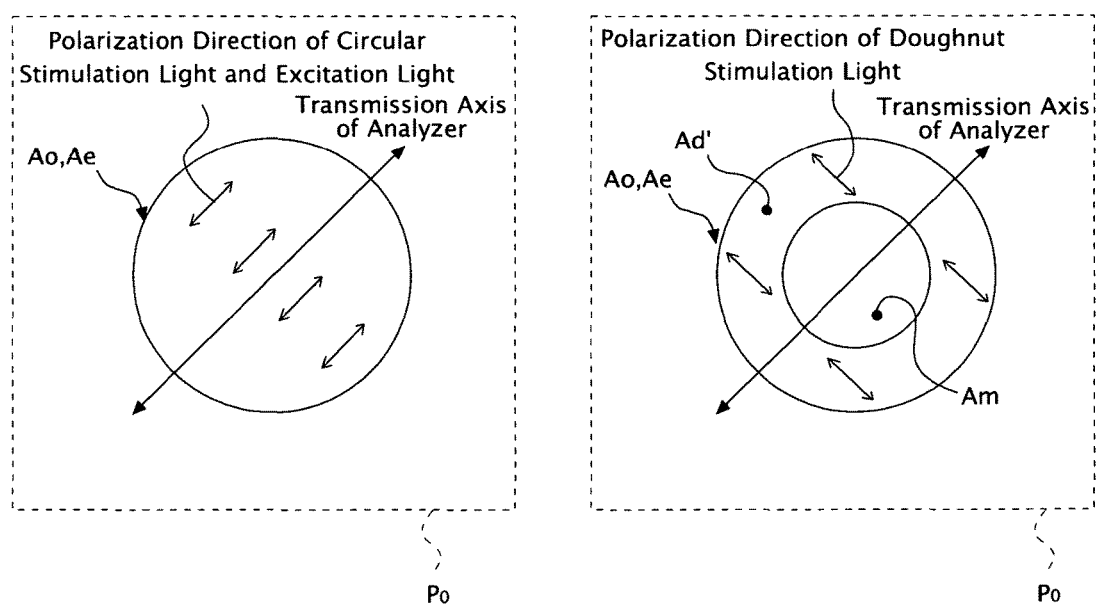
FIG. 8 is a diagram explaining polarized states of respective lights in the excitation light spot.

Further, in the stimulated emission microscopy of the modified example, an axis direction of the ¼ wavelength plate 60 is also adjusted beforehand, polarized states of the excitation light and the circular stimulation light heading toward the analyzer 70 are set to linear polarization in a predetermined direction as illustrated on the left side of FIG. 8, and a polarized state of the doughnut stimulation light heading toward the analyzer 70 is set to linear polarization in a direction perpendicular to the excitation light and the circular stimulation light as illustrated on the right side of FIG. 8.

Further, in the stimulated emission microscopy of the modified example, as illustrated in FIG. 8, a transmission axis direction of the analyzer 70 is set to the same direction as the polarization direction of the circular stimulation light and the excitation light to be incident on the analyzer 70 (namely, a direction perpendicular to the polarization direction of the doughnut stimulation light).

Accordingly, in the stimulated emission microscopy of the modified example, the doughnut stimulation light exited from the observation object plane $P_0$ is blocked before the light detector 24, and the circular stimulation light exited from the observation object plane $P_0$ is incident on the light detector 24.

Note that the polarization direction of the excitation light to be incident on the observation object plane $P_0$ is made to coincide with the polarization direction of the circular stimulation light to be incident on the observation object plane $P_0$ here, so that it is possible to increase efficiency of stimulated emission in the non-overlap region Am.

However, when it is not necessary to increase the efficiency of stimulated emission in the non-overlap region Am, it is not necessary to make the polarization direction of the excitation light to be incident on the observation object plane $P_0$ coincide with the polarization direction of the circular stimulation light to be incident on the observation object plane $P_0$.

Further, the polarized state of the doughnut stimulation light passing through the phase plate 18 is set to the circular polarization, thereby making it possible to make the doughnut stimulation light spot isotropic (rotationally symmetric about the optical axis).

However, when it is not necessary to make the doughnut stimulation light spot isotropic, the polarized state of the doughnut stimulation light passing through the phase plate 18 may be set to the linear polarization.

Note that in this case, it is only necessary to omit the ¼ wavelength plates 51 and 60 and set the polarized state of each of the excitation light to be incident on the observation object plane $P_0$, the doughnut stimulation light to be incident on the observation object plane $P_0$, and the circular stimulation light to be incident on the observation object plane $P_0$ to the linear polarization.

Also in this case, the polarization direction of the doughnut stimulation light only needs to be made perpendicular to the polarization direction of the circular stimulation light and the polarization direction of the excitation light before the light detector 24.

Supplements of First Embodiment and Modified Example

Note that although in the first embodiment and the modified example, the timing at which the excitation light reaches the observation object plane $P_0$, the timing at which the doughnut stimulation light reaches the observation object plane $P_0$, and the timing at which the circular stimulation light reaches the observation object plane $P_0$ are made to differ, at least two of these three timings may be made to coincide with each other.

For example, it is possible to emit the excitation light and the doughnut stimulation light to the observation object plane $P_0$ simultaneously, and then emit the circular stimulation light (note that $\omega_2' \neq \omega_2$ is satisfied).

Alternatively, it is also possible to emit the excitation light, the doughnut stimulation light, and the circular stimulation light simultaneously in a state where a wavelength difference of 3600 cm$^{-1}$ or more in terms of energy is provided between the excitation light and the circular stimulation light (note that $\omega_2' \neq \omega_2$ is satisfied).

Further, although the first embodiment and the modified example are ones in which the present invention is applied to the stimulated emission microscopy, the present invention is applicable also to an excited state absorption (ESA: excited state absorption) microscopy similarly.

In this case, the point that the light of the optical frequency $\omega_1$ with a circular light spot is used as the excitation light and the light of the optical frequency $\omega_2'$ with a doughnut-shaped light spot is used as the stimulation light is similar to the first embodiment or the modified example, but a photon energy of the other light with a circular light spot (the optical frequency $\omega_2$) is set to a value corresponding to an energy difference between a first excited state and a second excited state of the ESA. For example, the optical frequencies $\omega_1$ and $\omega_2'$ are set to be within a range of from ultraviolet region to visible region wavelengths approximately in terms of a wavelength, and the optical frequencies $\omega_2$ is set to be within a range of from visible region to near-infrared region wavelengths approximately in terms of a wavelength.

Further, although the first embodiment and the modified example are ones in which the present invention is applied to the stimulated emission microscopy, the present invention is applicable also to a GSD (Ground State Depletion) microscopy that depletes electrons in a ground state similarly.

In this case, the light of the optical frequency $\omega_1$ with a circular light spot, the light of the optical frequency $\omega_2'$ with a doughnut-shaped light spot, and the light of the optical frequency $\omega_2$ with a circular light spot are used, and these optical frequencies $\omega_1$, $\omega_2'$ and $\omega_2$ are set to a value such that excitation from a ground state to an excited state occurs. For example, the optical frequencies $\omega_1$, $\omega_2'$, and $\omega_2$ are each set to be within a range of from ultraviolet region to visible region wavelengths approximately in terms of a wavelength.

Further, although in the first embodiment and the modified example, it is not mentioned whether the excitation by means of the excitation light is one-photon excitation or multiphoton excitation, it may be one-photon excitation, or may also be multiphoton excitation. For example, when it is two-photon excitation, the optical frequency $\omega_1$ of the excitation light is desirably set to be within a range of from visible region to near-infrared region wavelengths in terms of a wavelength.

Second Embodiment

Hereinafter, there will be explained a CARS microscopy as a second embodiment of the present invention. Here, only differences from the first embodiment (FIG. 1) are explained.

Figure 9:
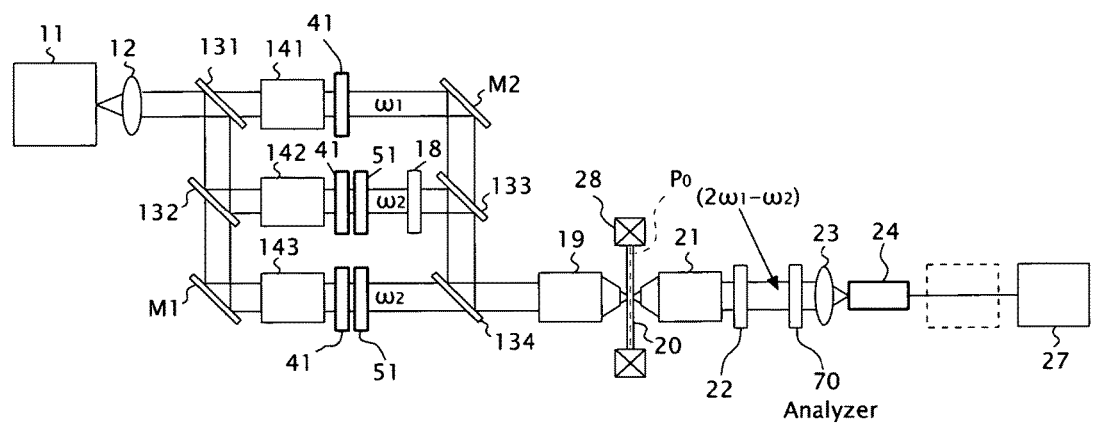
FIG. 9 is a configuration diagram of a CARS microscopy.

FIG. 9 is a configuration diagram of the CARS microscopy.

First, in the CARS microscopy, the optical frequency $\omega_2'$ of the doughnut stimulation light is set to be the same as the optical frequency $\omega_2$ of the circular stimulation light.

Further, in the CARS microscopy, a timing at which the excitation light (optical frequency $\omega_1$) is emitted to the observation object plane $P_0$, a timing at which the doughnut stimulation light (optical frequency $\omega_2$) reaches the observation object plane $P_0$, and a timing at which the circular stimulation light (optical frequency $\omega_2$) reaches the observation object plane $P_0$) are made to coincide with each other.

Further, in the CARS microscopy, pulse shapes (pulsed light intensities and pulse widths) of the respective excitation light, doughnut stimulation light, and circular stimulation light, and the optical frequencies $\omega_1$ and $\omega_2$ are set so as to cause a CARS process to occur in the observation object substance in the light spot of the observation object plane $P_0$ ($\omega_1 > \omega_2$). The pulse shapes of these lights can be adjusted by a shape of pulse oscillated by the pulsed laser light source 11, transmittance and reflectance of the beam splitter 131, and transmittance and reflectance of the beam splitter 132 (note that they may be adjusted by the transmittance of the aforementioned ND filter).

Further, an optical frequency of a signal light that should be detected by the CARS microscopy (CARS light) is ($2\omega_1 - \omega_2$), which is different from both the optical frequency ($\omega_1$) of the excitation light and the optical frequency ($\omega_2$) of the stimulation light, and therefore the signal generator 26, the acousto-optics modulator 15, and the lock-in amplifier 25 are not needed basically.

Instead, the wavelength selection filter 22 in the CARS microscopy includes wavelength-selectivity characteristics that cause the wavelength selection filter 22 to allow a light of the same optical frequency ($2\omega_1 - \omega_2$) as that of the CARS light to pass therethrough and block a light of the optical frequency $\omega_1$ and a light of the optical frequency $\omega_2$ provided thereto.

Further, the CARS light is weak, so that as the light detector 24 of the CARS microscopy, a high-sensitive light detector, for example, a photomultiplier tube (PMT: photomultiplier Tube) is desirably used.

Further, in the CARS microscopy of this embodiment, in order to enable super resolution, the polarizer 41 is disposed in the independent optical path of the excitation light, the polarizer 41 and the ¼ wavelength plate 51 are disposed in order in the independent optical path of the doughnut stimulation light, the polarizer 41 and the ¼ wavelength plate 51 are disposed in order in the independent optical path of the circular stimulation light, and the analyzer 70 is disposed between the objective lens 21 and the collecting lens 23.

Figure 10:
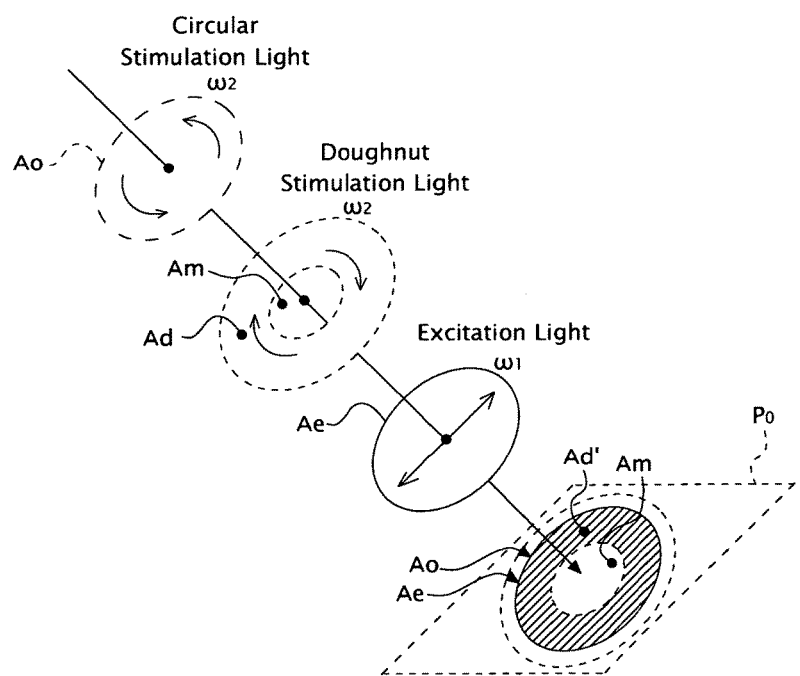
FIG. 10 is a diagram explaining a relation between the excitation light spot, the doughnut stimulation light spot, and the circular stimulation light spot in the CARS microscopy.

Further, in the CARS microscopy of this embodiment, axis directions of the polarizers 41 and the ¼ wavelength plates 51 are adjusted beforehand, and as illustrated in FIG. 10, a polarized state of the excitation light to be incident on the observation object plane $P_0$ is set to linear polarization in a predetermined direction, (which is set to linear polarization in a 0° direction, hereinafter), a polarized state of the doughnut stimulation light to be incident on the observation object plane $P_0$ is set to right-handed or left-handed circular polarization, (which is set to right-handed circular polarization, hereinafter), and a polarized state of the circular stimulation light to be incident on the observation object plane $P_0$ is set to circular polarization in which the circular stimulation light circles opposite to the doughnut stimulation light, (which is set to left-handed circular polarization, here).

Here, the doughnut stimulation light being a right-handed circularly polarized light and the circular stimulation light being a left-handed circularly polarized light are both incident on the overlap region Ad' of the observation object plane $P_0$, resulting in that the total polarized state of the stimulation lights in the overlap region Ad' becomes a combination of the doughnut stimulation light and the circular stimulation light.

However, a relation between an amplitude of the doughnut stimulation light heading toward the observation object plane $P_0$, a phase of the doughnut stimulation light heading toward the observation object plane $P_0$, an amplitude of the circular stimulation light heading toward the observation object plane $P_0$, and a phase of the circular stimulation light heading toward the observation object plane $P_0$ is adjusted beforehand so that a combined polarization direction of the doughnut stimulation light and the circular stimulation light that head toward the observation object plane $P_0$ becomes a 90° direction.

In the meantime, the doughnut stimulation light being a right-handed circularly polarized light is not incident on the non-overlap region Am, so that the total polarized state of the stimulation light in the non-overlap region Am is left-handed circular polarization.

Figure 11:
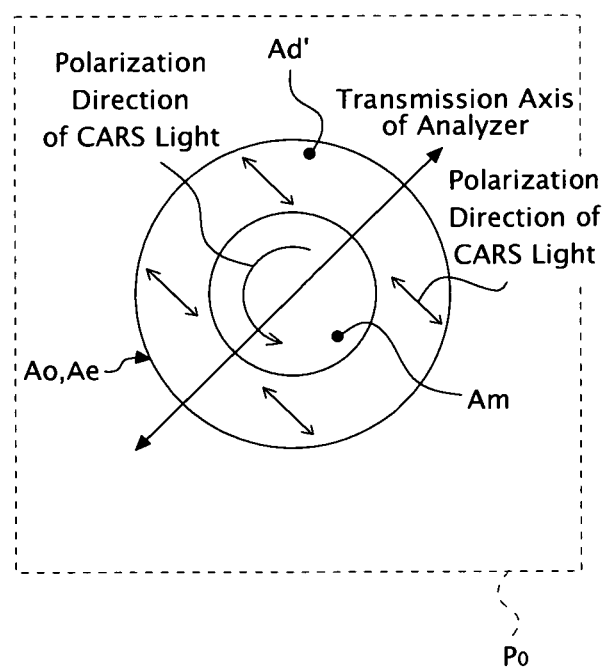
FIG. 11 is a diagram explaining polarized states of respective lights in the CARS microscopy.

Accordingly, in the CARS microscopy of this embodiment, as illustrated in FIG. 11, the CARS light (optical frequency $2\omega_1 - \omega_2$) generated in the non-overlap region Am results in a "left-handed circularly polarized light" that is the same as the stimulation light to work in the non-overlap region Am, while the CARS light (optical frequency $2\omega_1 - \omega_2$) generated in the overlap region Ad' results in a "linearly polarized light in the 90° direction" that is the same as the stimulation lights to work in the overlap region Ad'.

Thus, in the CARS microscopy of this embodiment, a transmission axis direction of the analyzer 70 is set the same as the polarization direction of the excitation light (the 0° direction, here) as illustrated in FIG. 11.

Accordingly, in the CARS microscopy of this embodiment, the CARS light generated in the overlap region Ad' is blocked before the light detector 24, and the CARS light generated in the non-overlap region Am is incident on the light detector 24.

Accordingly, in the CARS microscopy of this embodiment, it is possible to limit a detection origin of the CARS light only to the non-overlap region Am that is smaller than the resolution limit of the objective lens 19 (size of excitation light spot Ae). That is, in the CARS microscopy of this embodiment, a super-resolution observation of the sample 20 is enabled.

Note that the polarized state of the doughnut stimulation light passing through the phase plate 18 is set to the circular polarization here, thereby making it possible to make the doughnut stimulation light spot Ad isotropic (rotationally symmetric about the optical axis).

However, when it is not necessary to make the doughnut stimulation light spot Ad isotropic, it is also possible to set the polarized state of the doughnut stimulation light passing through the phase plate 18 to the linear polarization.

Note that in this case, it is only necessary to omit the ¼ wavelength plates 51 and set the polarized state of each of the excitation light to be incident on the observation object plane $P_0$, the doughnut stimulation light to be incident on the observation object plane $P_0$, and the circular stimulation light to be incident on the observation object plane $P_0$ to the linear polarization.

In this case, the polarization direction of the doughnut stimulation light to be incident on the observation object plane $P_0$ only needs to be made perpendicular to the polarization directions of the circular stimulation light and the excitation light to be incident on the observation object plane $P_0$.

Further, in the CARS microscopy, when the electrical signal output from the light detector 24 is weak, it is also possible to modulate the intensity of excitation light by means of the frequency $f_1$ over the time direction and at the same time, perform lock-in detection by means of the frequency $f_1$ or $2f_1$, to thereby increase detection accuracy of the CARS light. Note that a method of the lock-in detection is as has been described in the first embodiment.

Further, in the CARS microscopy of this embodiment, in order to block the CARS light from the overlap region Ad' before the light detector 24, the CARS light from the overlap region Ad' and the CARS light from the non-overlap region Am are polarization-separated.

In this embodiment, however, instead of polarization-separating the CARS light from the overlap region Ad' and the CARS light from the non-overlap region Am, "two-frequency lock-in" may be performed (see "Modified example of second embodiment").

Further, although the microscopy of this embodiment is a CARS microscopy in which the signal light of the optical frequency $(2\omega_1-\omega_2)$ (CARS light) is set as a detection object, as long as a signal light of an optical frequency $(2\omega_2-\omega_1)$ (CSRS light) is set as a detection object in place of the signal light of the optical frequency $(2\omega_1-\omega_2)$ (CARS light), a coherent stokes Raman scattering (CSRS: Coherent Stokes Raman scattering) microscopy is fabricated. This CSRS microscopy can also reflect molecular vibration of the non-overlap region Am with respect to the signal light (CSRS light) similarly to the CARS microscopy, thereby enabling an unstained super-resolution observation of the sample 20.

Modified Example of Second Embodiment

Hereinafter, as a modified example of the second embodiment, a two-frequency lock-in type CARS microscopy will be explained. Here, only differences from the second embodiment (FIG. 9) are explained.

Figure 12:
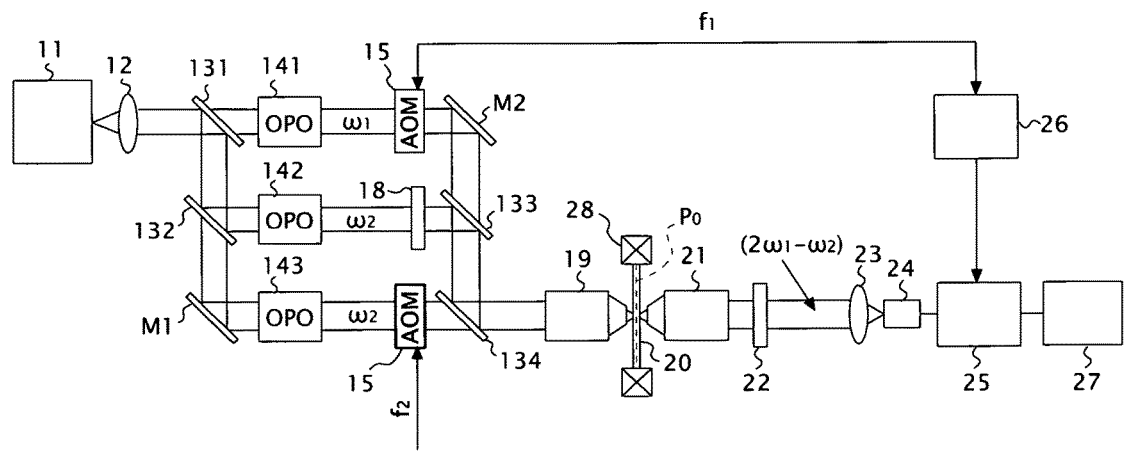
FIG. 12 is a configuration diagram of a two-frequency lock-in type CARS microscopy.

FIG. 12 is a configuration diagram of the two-frequency lock-in type CARS microscopy.

First, in the two-frequency lock-in type CARS microscopy, although the polarizers 41, the ¼ wavelength plates 51, and the analyzer 70 are omitted, the acousto-optics modulators 15, the signal generator 26, and the lock-in amplifier 25 are provided instead.

Further, in the two-frequency lock-in type CARS microscopy, the acousto-optics modulator 15 is disposed in both the independent optical path of the excitation light and the independent optical path of the circular stimulation light.

Further, the acousto-optics modulator 15 disposed in the optical path of the excitation light modulates the intensity of excitation light by means of the frequency $f_1$ over the time direction, and the acousto-optics modulator 15 disposed in the optical path of the circular stimulation light modulates the intensity of circular stimulation light by means of a frequency $f_2$ over the time direction (note that $f_1 \neq f_2$ is satisfied).

Figure 13:
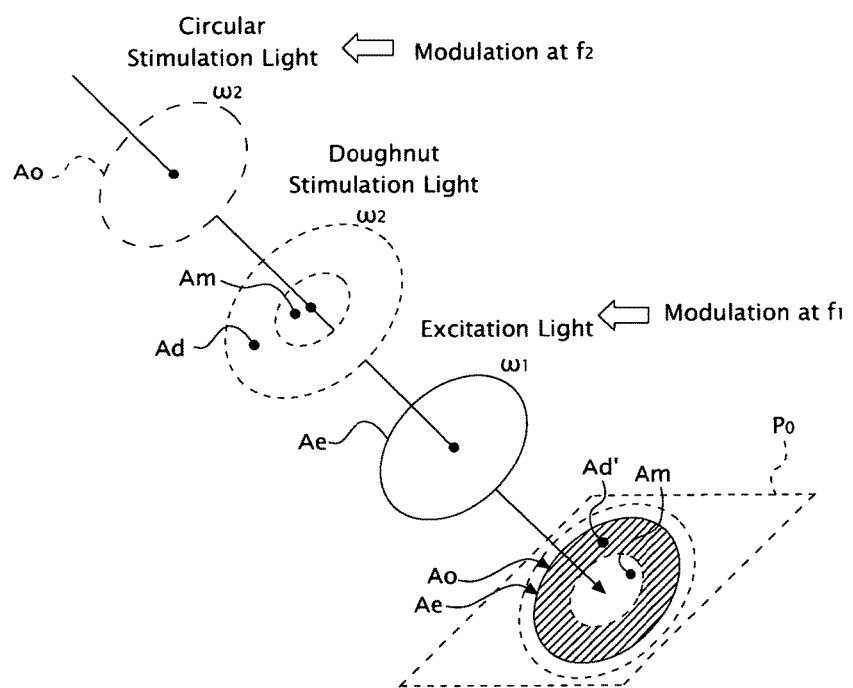
FIG. 13 is a diagram explaining a relation between the excitation light spot, the doughnut stimulation light spot, and the circular stimulation light spot in the two-frequency lock-in type CARS microscopy.

In the above two-frequency lock-in type CARS microscopy, as a light that causes the CARS process to occur, an excitation light modulated by means of the frequency $f_1$ and a circular stimulation light modulated by means of the frequency $f_2$ are incident on the non-overlap region Am of the observation object plane $P_0$ as illustrated in FIG. 13.

In the meantime, on the overlap region Ad' of the observation object plane $P_0$, as a light that causes the CARS process to occur, the excitation light modulated by means of the frequency $f_1$, the doughnut stimulation light that is not modulated, and the circular stimulation light modulated by means of the frequency $f_2$ are incident as illustrated in FIG. 13.

Figure 14:
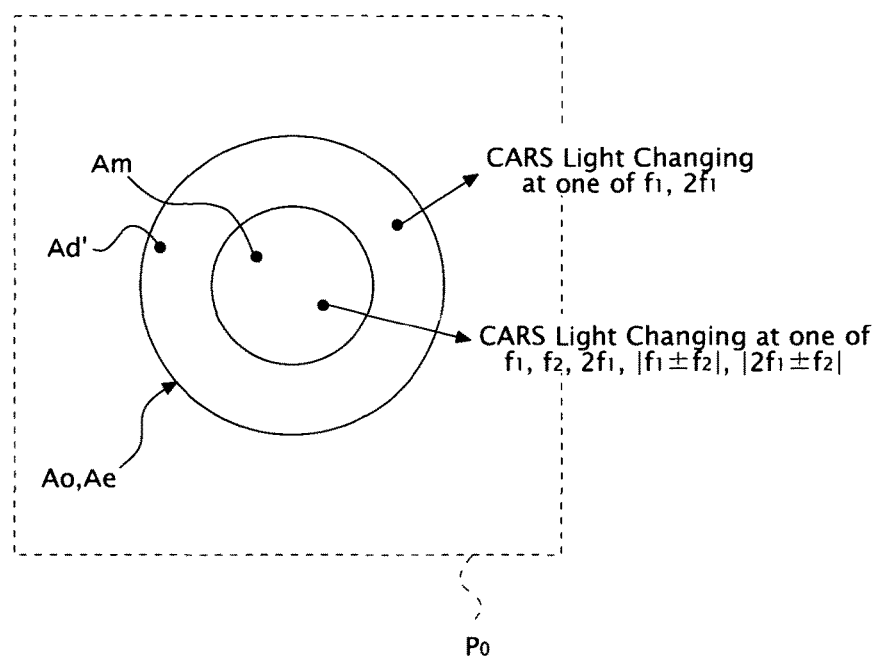
FIG. 14 is a diagram explaining modulation frequencies of respective lights in the two-frequency lock-in type CARS microscopy.

Therefore, in the two-frequency lock-in type CARS microscopy, as illustrated in FIG. 14, the CARS light (optical frequency $2\omega_1-\omega_2$) generated in the non-overlap region Am changes by means of one of the frequencies $f_1$, $f_2$, $2f_1$, $|f_1 \pm f_2|$ and $|2f_1 \pm f_2|$, and the CARS light (optical frequency $2\omega_1-\omega_2$) generated in the overlap region Ad' changes by means of one of the frequencies $f_1$ and $2f_1$.

Thus, the lock-in amplifier 25 in the two-frequency lock-in type CARS microscopy performs lock-in detection by means of one of the frequencies $f_2$, $|f_1 \pm f_2|$, and $|2f_1 \pm f_2|$, to thereby detect only the CARS light generated in the non-overlap region Am.

Accordingly, also in the two-frequency lock-in type CARS microscopy, it is possible to limit a detection origin of the CARS light only to the non-overlap region Am that is smaller than the resolution limit of the objective lens 19 (size of the excitation light spot Ae). That is, also in the two-frequency lock-in type CARS microscopy, a super-resolution observation of the sample 20 is enabled.

Note that in the two-frequency lock-in type CARS microscopy, a magnitude relation between the above-described frequencies $f_1$ and $f_2$ does not matter, but a combination of the frequencies $f_1$ and $f_2$ is desirably selected so that each of the frequencies $f_1$ and $f_2$ and the detection frequency of lock-in detection (one of the frequencies $f_2$, $|f_1 \pm f_2|$, and $|2f_1 \pm f_2|$) establish a non-integral multiple relation.

Further, the ¼ wavelength plate 51 is inserted in the output optical path of the optical parametric oscillator 142 and the polarized state of the doughnut stimulation light is set to the circular polarization, thereby making it possible to make the doughnut shape (an intensity distribution of the doughnut stimulation light spot) more isotropic.

Further, the CSRS microscopy explained in the second embodiment can also be transformed similarly to this modified example (namely, transformed into a two-frequency lock-in type). In this case, however, the detection frequency of lock-in detection is desirably set to one of $f_1$, $|f_2 \pm f_1|$, and $|2f_2 \pm f_1|$.

Third Embodiment

Hereinafter, there will be explained an SRS microscopy as a third embodiment of this embodiment. Here, only differences from the second embodiment (CARS microscopy in FIG. 9) are explained.

Figure 15:
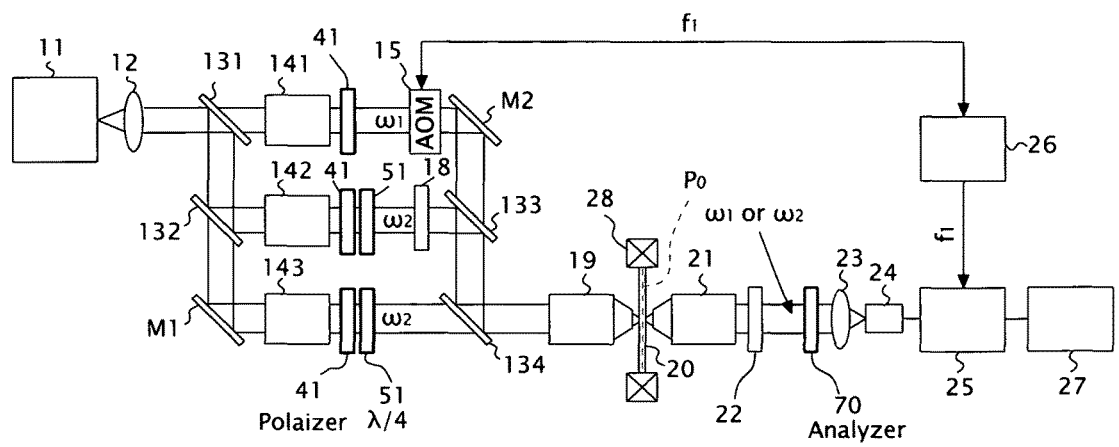
FIG. 15 is a configuration diagram of an SRS microscopy.

FIG. 15 is a configuration diagram of the SRS microscopy.

First, in the SRS microscopy, the pulse shapes (pulsed light intensities and pulse widths) of the respective excitation light, doughnut stimulation light, and circular stimulation light, and the optical frequencies $\omega_1$ and $\omega_2$ are set so as to cause an SRS process to occur in the observation object substance in the light spot of the observation object plane $P_0$ ($\omega_1 > \omega_2$). The pulse shapes of these lights can be adjusted by a shape of pulse oscillated by the pulsed laser light source 11, the transmittance and reflectance of the beam splitter 131, and the transmittance and reflectance of the beam splitter 132 (note that they may be adjusted by the transmittance of the aforementioned ND filter).

When the SRS process occurs in the light spot, intensities of lights exited from the light spot change. Specifically, the intensity of light of the optical frequency $\omega_1$ decreases and the intensity of light of the optical frequency $\omega_2$ decreases. Therefore, an optical frequency of a signal light that should be detected by the SRS microscopy (an SRS light) is $\omega_1$ or $\omega_2$. The optical frequency ($\omega_1$ or $\omega_2$) of this signal light is the same as the optical frequency ($\omega_1$) of the excitation light or the optical frequency ($\omega_2$) of the stimulation light, resulting in that the acousto-optics modulator 15, the signal generator 26, and lock-in detection by means of the lock-in amplifier 25 are needed. Note that a configuration example illustrated in FIG. 15 is a configuration example in the case where the optical frequency to be a detection object is set to $\omega_2$. When the optical frequency to be a detection object is set to $\omega_1$, in FIG. 15, the optical frequency $\omega_1$ may be replaced with $\omega_2$ and the optical frequency $\omega_2$ may be replaced with $\omega_1$ respectively. Note that the lock-in detection performed for eliminating an effect of a noise light of the same optical frequency as that of the signal light is publicly known, so that its explanation is omitted.

Further, the wavelength selection filter 22 in the SRS microscopy includes wavelength-selectivity characteristics that cause the wavelength selection filter 22 to allow a light of the same optical frequency ($\omega_1$ or $\omega_2$) as that of the SRS light to pass therethrough and block lights of optical frequencies different from that of the SRS slight provided thereto.

Figure 16:
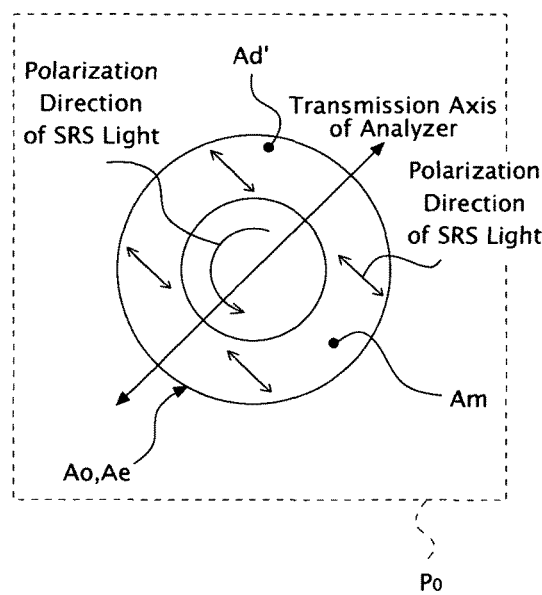
FIG. 16 is a diagram explaining polarized states of respective lights in the SRS microscopy.

Also in the above SRS microscopy, similarly to the second embodiment (CARS microscopy), as illustrated in FIG. 16, of the observation object plane $P_0$, a signal light generated in the overlap region Ad' (the SRS light, here) and a signal light generated in the non-overlap region Am (the SRS light, here) are shifted in a polarization direction. Therefore, also in the SRS microscopy, it is possible to separate the signal light generated in the non-overlap region Am (SRS light, here) from the signal light generated in the overlap region Ad' (SRS light, here).

Accordingly, also in the SRS microscopy, a super-resolution observation of the sample 20 is enabled similarly to the second embodiment (CARS microscopy).

Note that this embodiment can also be transformed similarly to the second embodiment (CARS microscopy). For example, in this embodiment, "two-frequency lock-in" may be performed instead of polarization-separating the SRS light from the overlap region Ad' and the SRS light from the non-overlap region Am (see a modified example below).

Modified Example of Third Embodiment

Hereinafter, there will be explained a two-frequency lock-in type SRS microscopy as a modified example of the third embodiment. Here, only differences from the third embodiment are explained.

Figure 17:
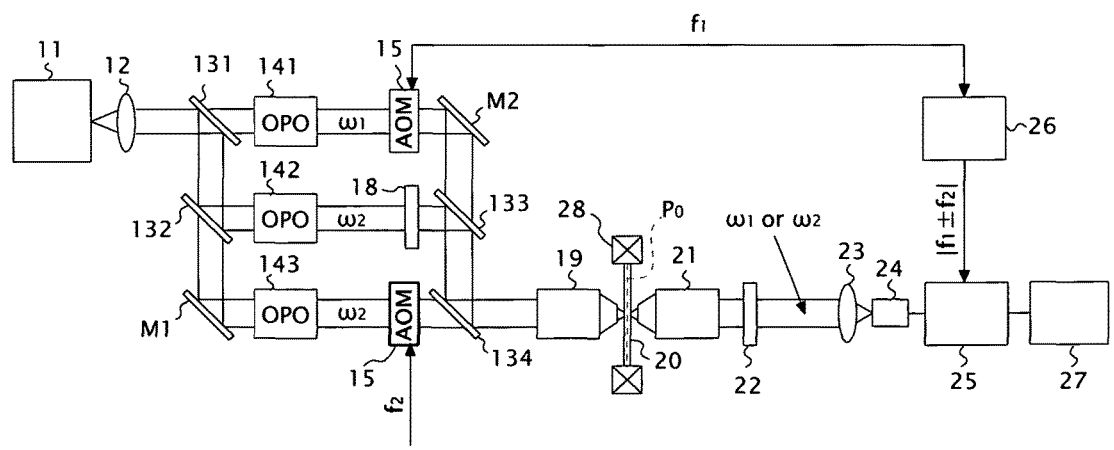
FIG. 17 is a configuration diagram of a two-frequency lock-in type SRS microscopy.

FIG. 17 is a configuration diagram of the two-frequency lock-in type SRS microscopy.

First, in the two-frequency lock-in type SRS microscopy, although the polarizers 41, the ¼ wavelength plates 51, and the analyzer 70 are omitted, the acousto-optics modulator 15 is disposed not only in the independent optical path of the excitation light but also in the independent optical path of the circular stimulation light instead.

Further, the acousto-optics modulator 15 disposed in the independent optical path of the excitation light modulates the intensity of excitation light by means of the frequency $f_1$ over the time direction, and the acousto-optics modulator 15 disposed in the independent optical path of the circular stimulation light modulates the intensity of circular stimulation light by means of the frequency $f_2$ over the time direction (note that $f_1 \neq f_2$ is satisfied).

In the above two-frequency lock-in type SRS microscopy, on the non-overlap region Am of the observation object plane $P_0$, an excitation light modulated by means of the frequency $f_1$ and a circular stimulation light modulated by means of the frequency $f_2$ are incident as a light that causes the SRS process to occur.

In the meantime, on the overlap region Ad' of the observation object plane $P_0$, the excitation light modulated by means of the frequency $f_1$, the doughnut stimulation light that is not modulated, and the circular stimulation light modulated by means of the frequency $f_2$ are incident as a light that causes the SRS process to occur.

Figure 18:
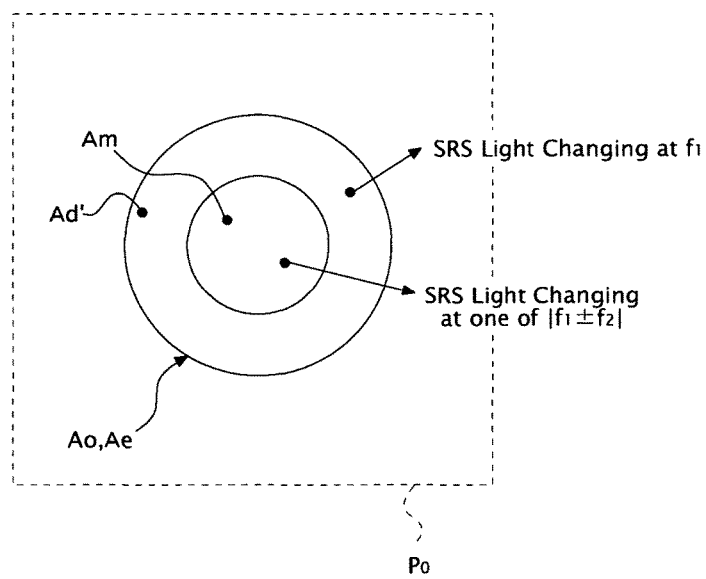
FIG. 18 is a diagram explaining modulation frequencies of respective lights in the two-frequency lock-in type SRS microscopy.

Therefore, in the two-frequency lock-in type SRS microscopy, as illustrated in FIG. 18, most of SRS signals generated in the non-overlap region Am (where the optical frequency of the SRS signal is set to $\omega_2$) change by means of the frequency $|f_1 \pm f_2|$, and most of SRS signals (optical frequency $\omega_2$) generated in the overlap region Ad' change by means of the frequency $f_1$.

Thus, in the two-frequency lock-in type SRS microscopy, the lock-in amplifier 25 performs lock-in detection by means of the frequency $|f_1 \pm f_2|$, to thereby detect the SRS light (optical frequency $\omega_2$) generated in the non-overlap region Am by separating from the SRS light (optical frequency $\omega_2$) generated in the overlap region Ad'.

Accordingly, also in the two-frequency lock-in type SRS microscopy, it is possible to limit a detection origin of the SRS light (optical frequency $\omega_2$) only to the non-overlap region Am that is smaller than the resolution limit of the objective lens 19 (size of the excitation light spot Ae). That is, also in the two-frequency lock-in type SRS microscopy, a super-resolution observation of the sample 20 is enabled.

Incidentally, although the optical frequency of the signal light (SRS light) is set to $\omega_2$, it goes without saying that it may be set to $\omega_1$.

Further, the ¼ wavelength plate 51 is inserted in the output optical path of the optical parametric oscillator 142 and the polarized state of the doughnut stimulation light is set to the circular polarization, thereby making it possible to make the doughnut shape (intensity distribution of the doughnut stimulation light spot) more isotropic.

Note that a magnitude relation between the above-described frequencies $f_1$ and $f_2$ does not matter, but a combination of the frequencies $f_1$ and $f_2$ is desirably selected so that each of the frequencies $f_1$ and $f_2$ and the detection frequency $|f_1 \pm f_2|$ of lock-in detection establish a non-integral multiple relation.

Fourth Embodiment

Hereinafter, there will be explained a two-photon absorption microscopy as a fourth embodiment of the present invention. Here, only differences from the third embodiment (SRS microscopy in FIG. 15) are explained.

Figure 19:
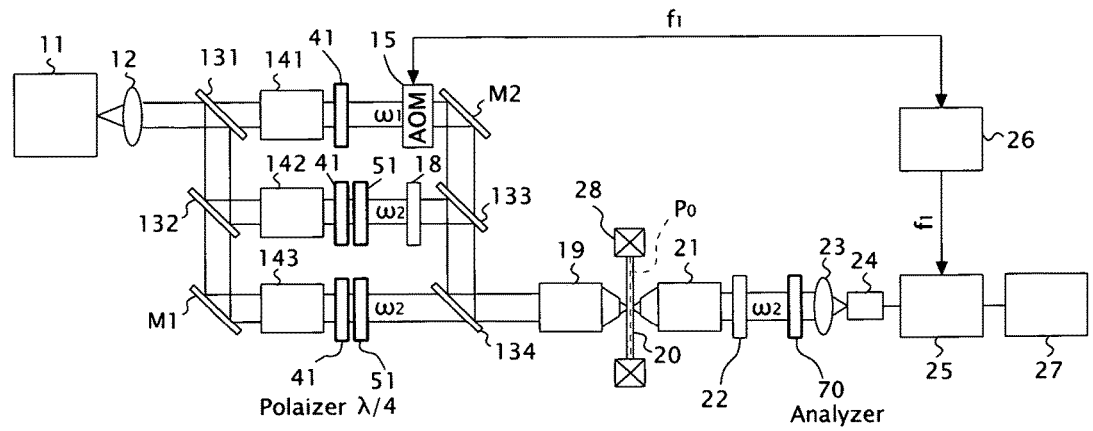
FIG. 19 is a configuration diagram of a two-photon absorption microscopy.

FIG. 19 is a configuration diagram of the two-photon absorption microscopy.

As illustrated in FIG. 19, a configuration of the two-photon absorption microscopy is basically the same as the configuration of the third embodiment (SRS microscopy).

However, in the two-photon absorption microscopy, the pulse shapes (pulsed light intensities and pulse widths) of the respective excitation light, doughnut stimulation light, and circular stimulation light, and the optical frequencies $\omega_1$ and $\omega_2$ are set so as to cause a two-photon absorption process to occur in the observation object substance in the light spot of the observation object plane $P_0$ ($\omega_1 > \omega_2$).

Further, an optical frequency of a signal light that should be detected by the two-photon absorption microscopy (decrease in light caused by two-photon absorption) is $\omega_2$, so that the wavelength selection filter 22 in the two-photon absorption microscopy includes wavelength-selectivity characteristics that cause the wavelength selection filter 22 to allow a light of the same optical frequency $\omega_2$ as that of the signal light (decrease in light caused by two-photon absorption) to pass therethrough and block a light of the optical frequency ($\omega_1$) different from that of the signal light (decrease in light caused by two-photon absorption) provided thereto.

Also in the above two-photon absorption microscopy, a super-resolution observation of the sample 20 is enabled similarly to the third embodiment (SRS microscopy).

Further, this embodiment can also be transformed similarly to the third embodiment (SRS microscopy). For example, in this embodiment, "two-frequency lock-in" may be performed instead of polarization-separating the signal light from the overlap region and the signal light from the non-overlap region (see a modified example below).

Modified Example of Fourth Embodiment

Hereinafter, there will be explained a two-frequency lock-in type two-photon absorption microscopy as a modified example of the fourth embodiment. Here, only differences from the fourth embodiment are explained.

Figure 20:
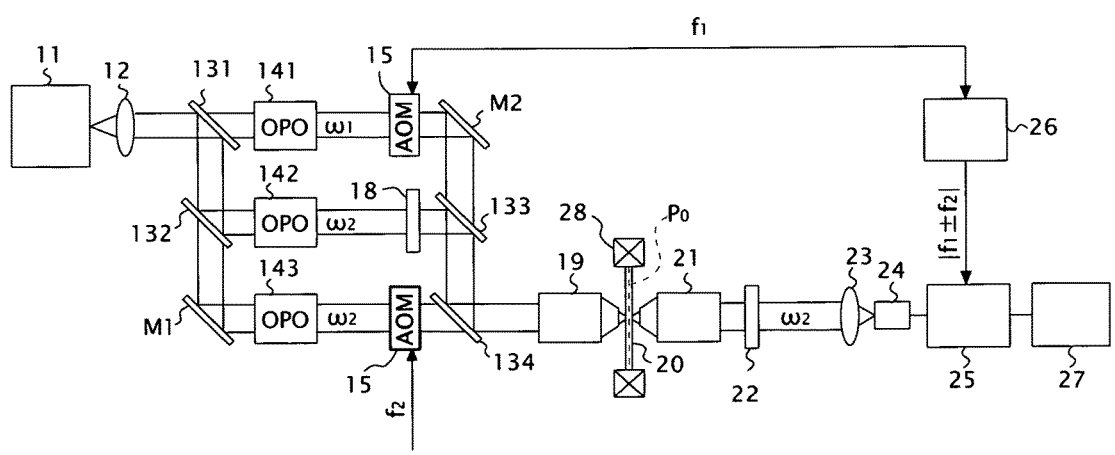
FIG. 20 is a configuration diagram of a two-frequency lock-in type two-photon absorption microscopy.

FIG. 20 is a configuration diagram of the two-frequency lock-in type two-photon absorption microscopy.

First, in the two-frequency lock-in type two-photon absorption microscopy, although the polarizers 41, the ¼ wavelength plates 51, and the analyzer 70 are omitted, the acousto-optics modulator 15 is disposed not only in the independent optical path of the excitation light but also in the independent optical path of the circular stimulation light instead.

Further, the acousto-optics modulator 15 disposed in the optical path of the excitation light modulates the intensity of excitation light by means of the frequency $f_1$ over the time direction, and the acousto-optics modulator 15 disposed in the optical path of the circular stimulation light modulates the intensity of circular stimulation light by means of the frequency $f_2$ over the time direction (note that $f_1 \neq f_2$ is satisfied).

Also in the above two-frequency lock-in type two-photon absorption microscopy, the lock-in amplifier 25 performs lock-in detection by means of the frequency $|f_1 \pm f_2|$, to thereby detect the signal light generated in the non-overlap region Am (decrease in light caused by two-photon absorption) by separating from the signal light generated in the overlap region Ad'.

Accordingly, also in the two-frequency lock-in type two-photon absorption microscopy, it is possible to limit a detection origin of the signal light (decrease in light caused by two-photon absorption) only to the non-overlap region Am that is smaller than the resolution limit of the objective lens 19 (size of the excitation light spot Ae). That is, also in the two-frequency lock-in type two-photon absorption microscopy, a super-resolution observation of the sample 20 is enabled.

Note that a magnitude relation between the above-described frequencies $f_1$ and $f_2$ does not matter, but a combination of the frequencies $f_1$ and $f_2$ is desirably selected so that each of the frequencies $f_1$ and $f_2$ and the detection frequency $|f_1 \pm f_2|$ of lock-in detection establish a non-integral multiple relation.

Further, the ¼ wavelength plate 51 is inserted in the output optical path of the optical parametric oscillator 142 and the polarized state of the doughnut stimulation light is set to the circular polarization, thereby making it possible to make the doughnut shape (intensity distribution of the doughnut stimulation light spot) more isotropic.

Supplements of Embodiments and Modified Examples

Note that in the above-described first embodiment to fourth embodiment or modified example, the size of non-overlap region Am in the observation object plane $P_O$ only needs to be made small in order to further increase a super-resolution effect (spatial resolution).

Further, in order to make the size of non-overlap region Am small, the intensity of doughnut stimulation light only needs to be increased. For achieving that, for example, the transmittance of the ND filter inserted in the independent optical path of the doughnut stimulation light only needs to be set high. Alternatively, the reflection ratios of the beam splitters 131 and 132 only need to be set high.

Incidentally, when polarization is utilized in one of the embodiments, there is a risk that as the intensity of doughnut stimulation light increases, orthogonality between polarization of the light from the overlap region Ad' and polarization of the light from the non-overlap region Am deteriorates, and a ratio of the signal from the non-overlap region Am decreases. Therefore, when polarization is utilized, an adjustment of the intensity of doughnut stimulation light is desirably performed appropriately while considering the polarized state of the light from the overlap region Ad'.

Further, although in the above-described embodiments, a combination of a single laser light source and three optical parametric oscillators is used in order to generate three laser lights with different optical paths, a combination of a single laser light source and two optical parametric oscillators may be used. In the case, however, a laser light exited from the laser light source as one of the three laser lights is used as it is.

Further, when the optical frequency $\omega_2$ and the optical frequency $\omega_2'$ are equal, the optical parametric oscillator that generates the light of the optical frequency $\omega_2$ and the optical parametric oscillator that generates the light of the optical frequency $\omega_2'$ may be commonalized.

Further, although in the above-described embodiments, the combination of a single laser light source and three optical parametric oscillators is used in order to generate three laser lights with different optical paths, two lights having different wavelengths may be extracted from a single optical parametric oscillator to be each utilized. In this case, however, when one optical frequency of the two lights is changed, the other optical frequency of the two lights changes with it, to therefore require attention.

Further, although in the above-described embodiments, a single laser light source and three optical parametric oscillators are used in order to generate three laser lights with different optical paths, three laser light sources may be used. In the case, however, the three laser light sources are desirably timing-synchronized.

Further, although in some of the above-described embodiments, the acousto-optics modulator 15 is used in order to modulate the intensity of pulsed laser light over the time direction, a combination of an electro-optic element and a polarizer may be used.

Further, although in some of the above-described embodiments, the acousto-optics modulator 15 is used in order to modulate the intensity of pulsed laser light over the time direction, a repetition frequency of the pulsed laser light may be controlled.

For example, in the first embodiment or the modified example, a repetition frequency frep1 of the pulsed laser light of the optical frequency $\omega_1$ may be set to 1/m times a repetition frequency frep2 of the pulsed laser light of the optical frequency $\omega_2$, and the detection frequency of lock-in detection may be set to frep1 (note that m is an integer of 2 or more).

Further, although in some of the above-described embodiments or modified examples (lock-in type), the intensity of light to be emitted to the sample 20 is modulated over the time direction, another property of the light to be emitted to the sample 20, which is, for example, one of phase, polarization, and optical frequency, may be modulated over the time direction.

Further, in some of the above-described embodiments or modified examples (lock-in type), in order to modulate the intensity of light to be emitted to the sample 20 over the time direction, the polarization of light heading toward the sample 20 may be modulated over the time direction and the analyzer may be disposed on an upstream side of the sample 20 in the optical path of the modulated light.

Incidentally, if the phase of light heading toward the sample 20 is modulated over the time direction in some of the above-described embodiments or modified examples (lock-in type), a pulse interval of the pulsed laser light to be emitted to the sample 20 changes in time.

Further, in some of the above-described embodiments or modified examples (lock-in type), whether or not the optical processes that cause changes in the energy level (stimulated emission, CARS, CSRS, SRS, two-photon absorption, and the like) occur, namely whether or not the signal light is generated depends on the optical frequency of the light to be emitted to the sample 20. Therefore, it is obvious that the optical frequency of the light to be emitted to the sample 20 is modulated over the time direction, and thereby the modulation is transcribed in the intensity of signal light. That is, it is obvious that the signal light can be lock-in detected.

Further, although in some of the above-described embodiments or modified examples (lock-in type), a property of one light of the three lights to be emitted to the sample 20 is modulated over the time direction, properties of at least two lights of the three lights may be modulated over the time direction by means of modulation frequencies different from each other.

Further, although in one of the above-described embodiments or modified examples, the transmission-type microscopy is explained, the present invention is applicable also to a reflection-type microscopy.

Further, although in the above-described first to fourth embodiments or modified examples, the number of light spots to be formed on the observation object plane $P_O$ simultaneously (namely, the number of observation object points) is set to be singular, it may be set to be plural. When the number of observation object points is made plural, it is possible to shorten a time taken for scanning the entire observation object plane $P_O$ at light spots (observation object points).

Further, although in the above-described first to fourth embodiments or modified examples, the shape of light spot in an in-plane direction is set to a doughnut shape in order to improve in-plane resolution, the shape of light spot in the optical axis direction may be set to a doughnut shape in order to improve resolution in the optical axis direction. In order to achieve it, it is only necessary to use a phase plate 18' in which a phase difference $\pi$[rad] is provided between a central circular region and a peripheral ring region (the phase plate 18' is not illustrated). High sectioning ability (the resolution in the optical axis direction) can be obtained in the above-described first to fourth embodiments or modified examples because where the aforementioned stimulated emission, excited state absorption, GSD, two-photon absorption, SRS, CARS, and CSRS occur is limited only to a collecting point with a high light intensity, and the sectioning ability further improves by applying this method.

Further, a combination of a light with a light spot doughnut-shaped in the in-plane direction (generated by the phase plate 18) and a light with a light spot doughnut-shaped in the optical axis direction (generated by the phase plate 18') may be used as the doughnut stimulation light. In this case, a super-resolution effect can be obtained over both the in-plane direction and the optical axis direction.

In order to realize it, a light that is subjected to a phase change by the phase plate 18 and a light that is subjected to a phase change by the phase plate 18' may be combined by an optical composite element such as a beam splitter or polarization beam splitter and a combined light may be collected onto a sample by an objective lens.

Further, although in the above-described first to fourth embodiments or modified examples, the case where the present invention is applied to the observation of an unstained sample is explained, the present invention is applicable also to observations of other samples such as a stained fluorescent sample and a stained non-fluorescent sample. Further, the present invention is applicable not only to the bio-observation but also to various observations such as material observation, for example.

Operation and Effect of Embodiments

One of the above-described embodiments or modified examples (stimulated emission microscopy, CARS microscopy, CSRS microscopy, SRS microscopy, and two-photon absorption microscopy) includes illumination optical system (the pulsed laser light source 11, the optical parametric oscillators 141, 142, and 143, the phase plate 18, and the objective lens 19) that collect a first illuminating light with a first optical frequency $\omega_1$ (the excitation light) onto a first region (the excitation light spot Ae) of an observation object (the sample 20), collect a second illuminating light with a second optical frequency $\omega_2'$ (the doughnut stimulation light) onto a second region (the doughnut stimulation light spot Ad) partially overlapping the first region (illumination region Ae), and collect a third illuminating light with a third optical frequency $\omega_2$ (the circular stimulation light) onto a third region (the circular stimulation light spot Ao) containing a non-overlap region (Am), the non-overlap region being a region of the first region (excitation light spot Ae) that does not overlap the second region (doughnut stimulation light spot Ad); and an extraction unit (the acousto-optics modulator 15, the signal generator 26, the lock-in amplifier 25, the polarizer 41, the ¼ wavelength plate 51, the wavelength selection filter 22, the ¼ wavelength plate 60, an analyzer 70, and the like) that extracts, from lights generated in a union (the light spot) of the first region (excitation light spot Ae), the second region (doughnut stimulation light spot Ad), and the third region (circular stimulation light spot Ao), signal lights generated in accordance with changes in an energy level of a substance present in the non-overlap region (Am) (the stimulated emission light, the CARS light, the SRS light, and the decrease in light caused by two-photon absorption).

Accordingly, one of the above-described embodiments or modified examples (stimulated emission microscopy, CARS microscopy, CSRS microscopy, SRS microscopy, and two-photon absorption microscopy) can set the non-overlap region (Am) that is smaller than a resolution limit of the illumination optical system (the size of excitation light spot Ae) as a detection origin of the signal light (stimulated emission light, CARS light, CSRS light, SRS light, and decrease in light caused by two-photon absorption).

Further, in the first embodiment or the modified example (stimulated emission microscopy), the illumination optical system (pulsed laser light source 11, optical parametric oscillators 141, 142, and 143, phase plate 18, and objective lens 19) emit the first illuminating light (excitation light), the second illuminating light (doughnut stimulation light), and the third illuminating light (circular stimulation light) to the observation object (sample 20) in order, and the extraction unit (acousto-optics modulator 15, signal generator 26, lock-in amplifier 25, polarizer 41, ¼ wavelength plate 51, wavelength selection filter 22, and analyzer 70) extracts the signal light with an optical frequency $\omega_2$ (stimulated emission light).

Further, in the first embodiment (stimulated emission microscopy), the extraction unit (signal generator 26 and lock-in amplifier 25) modulates a property of the first illuminating light (excitation light) heading toward the observation object (sample 20) over a time direction by means of a frequency $f_1$, and at the same time, lock-in detects the light generated in the unit (light spot) by means of the frequency $f_1$, thereby limiting a generation origin of the extracted signal light (stimulated emission light) only to the non-overlap region (Am).

Further, in the first embodiment (stimulated emission microscopy), the illumination optical system emit the first illuminating light (excitation light) and the second illuminating light (doughnut stimulation light) simultaneously, and then emit the third illuminating light (circular stimulation light), or emit the first illuminating light (excitation light), the second illuminating light (doughnut stimulation light), and the third illuminating light (circular stimulation light) simultaneously in a state where a wavelength difference of 3600 cm$^{-1}$ or more in terms of energy is provided between the first illuminating light (excitation light) and the third illuminating light (circular stimulation light), and the extraction unit extracts the signal light with the optical frequency $\omega_2$.

Further, in the super-resolution observation device of the first embodiment (stimulated emission microscopy), the extraction unit (optical parametric oscillators 142 and 143, and wavelength selection filter 22) provides, between the second illuminating light (doughnut stimulation light) and the third illuminating light (circular stimulation light) that head toward the observation object (sample 20), an optical frequency difference, and at the same time, blocks a light of the same optical frequency ($\omega_2'$) as that of the second illuminating light (doughnut stimulation light) on a downstream side of the observation object (sample 20), to thereby suppress mixture of the second illuminating light (doughnut stimulation light) into the extracted signal light (stimulated emission light).

Further, in the modified example of the first embodiment (stimulated emission microscopy), the extraction unit (polarizer 41 and analyzer 70) provides, between the second illuminating light (doughnut stimulation light) and the third illuminating light (circular stimulation light) that head toward the observation object (sample 20), a polarization direction difference, and at the same time, blocks a light in the same polarization direction as that of the second illuminating light (doughnut stimulation light) on the downstream side of the observation object (sample 20), to thereby suppress mixture of the second illuminating light (doughnut stimulation light) into the extracted signal light (stimulated emission light).

Further, in the second embodiment or the modified example (CARS microscopy), the illumination optical system (pulsed laser light source 11, optical parametric oscillators 141, 142, and 143, and objective lens 19) emit the first illuminating light (excitation light), the second illuminating light (doughnut stimulation light), and the third illuminating light (circular stimulation light) to the observation object (sample 20) simultaneously, and the extraction unit (wavelength selection filter 22) extracts the signal light with an optical frequency $(2\omega_1-\omega_2)$ (CARS light).

Further, in the second embodiment (CARS microscopy), the extraction unit (polarizer 41 and analyzer 70) provides, between the second illuminating light (doughnut stimulation light) and the third illuminating light (circular stimulation light) that head toward the observation object (sample 20), a polarization direction difference, and at the same time, blocks a light in the same polarization direction as a combined polarization direction of the second illuminating light (doughnut stimulation light) and the third illuminating light (circular stimulation light) on the downstream side of the observation object (sample 20), to thereby limit a generation origin of the extracted signal light (CARS light) only to the non-overlap region (Am).

Further, in the modified example of the second embodiment (two-frequency lock-in type CARS microscopy), the extraction unit (acousto-optics modulator 15, signal generator 26, and lock-in amplifier 25) modulates a property of the first illuminating light (excitation light) heading toward the observation object (sample 20) over the time direction by means of the frequency $f_1$ and modulates a property of the third illuminating light (circular stimulation light) heading toward the observation object (sample 20) over the time direction by means of a frequency $f_2$, and at the same time, lock-in detects the light generated in the union (light spot) by means of one of the frequencies $f_2$, $|f_1 \pm f_2|$, and $|2f_1 \pm f_2|$, to thereby limit a generation origin of the extracted signal light (CARS light) only to the non-overlap region (Am).

Further, in the modified example of the second embodiment (CSRS microscopy), the illumination optical system (pulsed laser light source 11, optical parametric oscillators 141, 142, and 143, and objective lens 19) emit the first illuminating light (excitation light), the second illuminating light (doughnut stimulation light), and the third illuminating light (circular stimulation light) to the observation object (sample 20) simultaneously, and the extraction unit (wavelength selection filter 22) extracts the signal light with the optical frequency $(2\omega_1-\omega_2)$ (CSRS light).

Further, in the second embodiment (CSRS microscopy), the extraction unit (polarizer 41 and analyzer 70) provides, between the second illuminating light (doughnut stimulation light) and the third illuminating light (circular stimulation light) that head toward the observation object (sample 20), a polarization direction difference, and at the same time, blocks a light in the same polarization direction as a combined polarization direction of the second illuminating light (doughnut stimulation light) and the third illuminating light (circular stimulation light) on the downstream side of the observation object (sample 20), to thereby limit a generation origin of the extracted signal light (CSRS light) only to the non-overlap region (Am).

Further, in the modified example of the second embodiment (two-frequency lock-in type CSRS microscopy), the extraction unit (acousto-optics modulator 15, signal generator 26, and lock-in amplifier 25) modulates a property of the first illuminating light (excitation light) heading toward the observation object (sample 20) over the time direction by means of the frequency $f_1$ and modulates a property of the third illuminating light (circular stimulation light) heading toward the observation object (sample 20) over the time direction by means of the frequency $f_2$, and at the same time, lock-in detects the light generated in the union (light spot) by means of one of the frequencies $f_1$, $|f_2 \pm f_1|$, and $|2f_2 \pm f_1|$, to thereby limit a generation origin of the extracted signal light (CSRS light) only to the non-overlap region (Am).

Further, in the third embodiment or the fourth embodiment and the modified example (SRS microscopy or two-photon absorption microscopy), the illumination optical system (pulsed laser light source 11, optical parametric oscillators 141, 142, and 143, phase plate 18, and objective lens 19) emit the first illuminating light (excitation light), the second illuminating light (doughnut stimulation light), and the third illuminating light (circular stimulation light) to the observation object (sample 20) simultaneously, and the extraction unit (acousto-optics modulator 15, signal generator 26, lock-in amplifier 25, polarizer 41, ¼ wavelength plate 51, wavelength selection filter 22, and analyzer 70) extracts the signal light with the optical frequency $\omega_2$ or $\omega_1$ (SRS light or decrease in light caused by two-photon absorption).

Further, in the third embodiment or the fourth embodiment (SRS microscopy or two-photon absorption microscopy), the extraction unit (polarizer 41 and analyzer 70) provides, between the second illuminating light (doughnut stimulation light) and the third illuminating light (circular stimulation light) that head toward the observation object (sample 20), a polarization direction difference, and at the same time, blocks a light in the same polarization direction as a combined polarization direction of the second illuminating light (doughnut stimulation light) and the third illuminating light (circular stimulation light) on the downstream side of the observation object (sample 20), to thereby limit a generation origin of the extracted signal light (SRS light or decrease in light caused by two-photon absorption) only to the non-overlap region (Am).

Further, in the modified example of the third embodiment or fourth embodiment (two-frequency lock-in type SRS microscopy or two-frequency lock-in type two-photon absorption microscopy), the extraction unit (acousto-optics modulator 15, signal generator 26, and lock-in amplifier 25) modulates a property of the first illuminating light (excitation light) heading toward the observation object (sample 20) over the time direction by means of the frequency $f_1$ and modulates a property of the third illuminating light (circular stimulation light) heading toward the observation object (sample 20) over the time direction by means of the frequency $f_2$, and at the same time, lock-in detects the light generated in the union (light spot) by means of the frequency $|f_1 \pm f_2|$, to thereby limit a generation origin of the extracted signal light (SRS light or decrease in light caused by two-photon absorption) only to the non-overlap region (Am).

Further, in one of the above-described embodiments or modified examples (lock-in type), the property being an object modulated by the extraction unit (acousto-optics modulator 15, signal generator 26, and lock-in amplifier 25) is one of the intensity, phase, polarization, and optical frequency of the light.

Further, in one of the above-described embodiments or modified examples (stimulated emission microscopy, CARS microscopy, CSRS microscopy, SRS microscopy, and two-photon absorption microscopy), shapes of the first region (excitation light spot Ae) and the third region (circular stimulation light spot Ao) are circular, a shape of the second region (doughnut stimulation light spot Ad) is a ring-belt shape, and a center of the first region (excitation light spot Ae), a center of the second region (doughnut stimulation light spot Ad), and a center of the third region (circular stimulation light spot Ao) coincide with each other.

Accordingly, one of the above-described super-resolution observation devices or modified examples (stimulated emission microscopy, CARS microscopy, CSRS microscopy, SRS microscopy, and two-photon absorption microscopy) can make the observation object point (non-overlap region Am) become smaller than the resolution limit of the illumination optical system (size of the excitation light spot Ae).

According to the present invention, the super-resolution observation device and the super-resolution observation method that are capable of performing a super-resolution observation on a sample without staining the sample are realized.

The many features and advantages of the embodiments are apparent from the detailed specification and, thus it is intended by the appended claims to cover all such features and advantages of the embodiments that fall within the true spirit and scope thereof. Further, since numerous modifications and changes will readily occur to those skilled in the art, it is not desired to limit the inventive embodiment to the exact construction and operation illustrated and described, and accordingly all suitable modifications and equivalents may be resorted to, falling within the scope thereof.

What is claimed is:

1. An observation device, comprising:
an illumination optical system configured to collect (i) a first illuminating light, which has a first optical frequency $\omega_1$, on a first region of an observation object, (ii) a second illuminating light, which has having a second optical frequency $\omega_2'$, on a second region partially overlapping the first region, and (iii) a third illuminating light, which has a third optical frequency $\omega_2$, on a third region that contains a non-overlap region, which is a region of the first region that does not overlap the second region; and
an extraction unit configured to extract a signal light, which has an optical frequency $\omega_2$ and is generated in accordance with a change in an energy level of a substance of the observation object in the non-overlap region, from light generated in all of the first region, the second region, and the third region, wherein:
the illumination optical system is configured to sequentially emit the first illuminating light, the second illuminating light, and the third illuminating light to the observation object; and
the extraction unit is configured (i) to modulate a property of the first illuminating light heading toward the observation object at a frequency $f_1$ to a time direction and (ii) to limit a generation origin of the signal light to be extracted to the non-overlap region by lock-in detecting the light generated in all of the first, second, and third regions at the frequency $f_1$.

2. The observation device according to claim 1, wherein:
the extraction unit is configured to provide an optical frequency difference between the second illuminating light and the third illuminating light heading toward the observation object, and
the extraction unit is configured to prevent a mixture of the second illuminating light into the signal light to be extracted by blocking a light at the second optical frequency $\omega_2'$ at a downstream side of the observation object.

3. The observation device according to claim 1, wherein:
the extraction unit is configured to provide a polarization direction difference between the second illuminating light and the third illuminating light heading toward the observation object, and
the extraction unit is configured to prevent a mixture of the second illuminating light into the signal light to be extracted by blocking a light in the same polarization direction as a polarization direction of the second illuminating light at a downstream side of the observation object.

4. The observation device according to claim 1, wherein the modulated property of the first illuminating light is one of an intensity, a phase, polarization, and an optical frequency of the light.

5. The observation device according to claim 1, wherein:
shapes of the first region and the third region are circular;
a shape of the second region is a ring-belt shape; and
a center of the first region, a center of the second region, and a center of the third region coincide with each other.

6. An observation method, comprising:
collecting a first illuminating light, which has a first optical frequency $\omega_1$, on a first region of an observation object;
collecting a second illuminating light, which has a second optical frequency $\omega_2'$, on a second region partially overlapping the first region;
collecting a third illuminating light, which has a third optical frequency $\omega_1$, on a third region containing that contains a non-overlap region, which is a region of the first region that does not overlap the second region;
extracting a signal light, which has an optical frequency $\omega_2$ and is generated in accordance with a change in an energy level of a substance of the observation object in the non-overlap region, from light generated in all of the first region, the second region, and the third region;
sequentially emitting the first illuminating light, the second illuminating light, and the third illuminating light to the observation object;
modulating a property of the first illuminating light heading toward the observation object at a frequency $f_1$ to a time direction; and
limiting a generation origin of the signal light to be extracted to the non-overlap region by lock-in detecting the light generated in all of the first, second, and third regions at the frequency $f_1$.

7. An observation device, comprising:
an illumination optical system configured to collect (i) a first illuminating light, which has a first optical frequency $\omega_1$, on a first region of an observation object, (ii) a second illuminating light, which has a second optical frequency $\omega_2'$, on a second region partially overlapping the first region, and (iii) a third illuminating light, which has a third optical frequency $\omega_2$, on a third region that contains a non-overlap region, which is a region of the first region that does not overlap the second region; and
an extraction unit configured to extract a signal light, which has an optical frequency $\omega_2$ and is generated in accordance with a change in an energy level of a substance of the observation object in the non-overlap region, from light generated in all of the first region, the second region, and the third region, wherein the illumination optical system is configured to emit either (i) the third illuminating light after emitting the first illuminating light and the second illuminating light simultaneously or (ii) the first illuminating light, the second illuminating light, and the third illuminating light simultaneously in a state where a wavelength difference of 3600 cm$^{-1}$ or more is provided between the first illuminating light and the third illuminating light.

8. The observation device according to claim 7, wherein:
the extraction unit is configured to provide an optical frequency difference between the second illuminating light and the third illuminating light heading toward the observation object, and
the extraction unit is configured to prevent a mixture of the second illuminating light into the signal light to be extracted by blocking a light at the second optical frequency $\omega_2'$ at a downstream side of the observation object.

9. The observation device according to claim 7, wherein:
the extraction unit is configured to provide a polarization direction difference between the second illuminating light and the third illuminating light heading toward the observation object, and
the extraction unit is configured to prevent a mixture of the second illuminating light into the signal light to be extracted by blocking a light in the same polarization direction as a polarization direction of the second illuminating light at a downstream side of the observation object.

10. An observation device, comprising:
an illumination optical system configured to collect (i) a first illuminating light, which has a first optical frequency $\omega_1$, on a first region of an observation object, (ii) a second illuminating light, which has a second optical frequency $\omega_2'$, on a second region partially overlapping the first region, and (iii) a third illuminating light, which has a third optical frequency $\omega_2$, on a third region that contains a non-overlap region, which is a region of the first region that does not overlap the second region; and
an extraction unit configured to extract a signal light, which has an optical frequency $(2\omega_1-\omega_2)$ and is generated in accordance with a change in an energy level of a substance of the observation object in the non-overlap region, from light generated in all of the first region, the second region, and the third region, wherein
the illumination optical system is configured to simultaneously emit the first illuminating light, the second illuminating light, and the third illuminating light to the observation object.

11. The observation device according to claim 10, wherein:
the extraction unit is configured to provide a polarization direction difference between the second illuminating light and the third illuminating light heading toward the observation object, and
the extraction unit is configured to limit a generation origin of the signal light to be extracted to the non-overlap region by blocking a light in the same polarization direction as a combined polarization direction of the second illuminating light and the third illuminating light at a downstream side of the observation object.

12. The observation device according to claim 10, wherein the extraction unit is configured (i) to modulate a property of the first illuminating light heading toward the observation object at a frequency $f_1$ to a time direction, (ii) to modulate a property of the third illuminating light heading toward the observation object at a frequency $f_2$ to the time direction, and (iii) to limit a generation origin of the signal light to be extracted to the non-overlap region by lock-in detecting the light generated in all of the first, second, and third regions at one of frequencies $f_2$, $|f_1 \pm f_2|$, and $|2f_1 \pm f_2|$.

13. An observation device, comprising:

an illumination optical system configured to collect (i) a first illuminating light, which has a first optical frequency $\omega_1$, on a first region of an observation object, (ii) a second illuminating light, which has a second optical frequency $\omega_2'$, on a second region partially overlapping the first region, and (iii) a third illuminating light, which has a third optical frequency $\omega_2$, on a third region that contains a non-overlap region, which is a region of the first region that does not overlap the second region; and an extraction unit configured to extract a signal light, which has an optical frequency $(2\omega_2 - \omega_1)$ and is generated in accordance with a change in an energy level of a substance of the observation object in the non-overlap region, from light generated in all of the first region, the second region, and the third region, wherein the illumination optical system is configured to simultaneously emit the first illuminating light, the second illuminating light, and the third illuminating light to the observation object.

14. The observation device according to claim 13, wherein:

the extraction unit is configured to provide a polarization direction difference between the second illuminating light and the third illuminating light heading toward the observation object, and the extraction unit is configured to limit a generation origin of the signal light to be extracted to the non-overlap region by blocking a light in the same polarization direction as a combined polarization direction of the second illuminating light and the third illuminating light at a downstream side of the observation object.

15. The observation device according to claim 13, wherein the extraction unit is configured (i) to modulate a property of the first illuminating light heading toward the observation object at a frequency $f_1$ to a time direction, (ii) to modulate a property of the third illuminating light heading toward the observation object at a frequency $f_2$ to the time direction, and (iii) to limit a generation origin of the signal light to be extracted to the non-overlap region by lock-in detecting the light generated in all of the first, second, and third regions at one of frequencies $f_1$, $|f_2 \pm f_1|$, and $|2f_2 \pm f_1|$.

16. An observation device, comprising:

an illumination optical system configured to collect (i) a first illuminating light, which has a first optical frequency $\omega_1$, on a first region of an observation object, (ii) a second illuminating light, which has a second optical frequency $\omega_2'$, on a second region partially overlapping the first region, and (iii) a third illuminating light, which has a third optical frequency $\omega_2$, on a third region that contains a non-overlap region, which is a region of the first region that does not overlap the second region; and an extraction unit configured to extract a signal light, which has an optical frequency of one of $\omega_2$ and $\omega_1$ and is generated in accordance with a change in an energy level of a substance of the observation object in the non-overlap region, from light generated in all of the first region, the second region, and the third region, wherein the illumination optical system is configured to simultaneously emit the first illuminating light, the second illuminating light, and the third illuminating light to the observation object.

17. The observation device according to claim 16, wherein:

the extraction unit is configured to provide a polarization direction difference between the second illuminating light and the third illuminating light heading toward the observation object, and the extraction unit is configured to limit a generation origin of the signal light to be extracted to the non-overlap region by blocking a light in the same polarization direction as a combined polarization direction of the second illuminating light and the third illuminating light at a downstream side of the observation object.

18. The observation device according to claim 16, wherein the extraction unit is configured (i) to modulate a property of the first illuminating light heading toward the observation object at a frequency $f_1$ to a time direction, (ii) to modulate a property of the third illuminating light heading toward the observation object at a frequency $f_2$ to the time direction, and (iii) to limit a generation origin of the signal light to be extracted to the non-overlap region by lock-in detecting the light generated in all of the first, second, and third regions at a frequency $|f_1 \pm f_2|$.

* * * * *